(12) United States Patent
Ibrahim et al.

(10) Patent No.: US 10,857,382 B2
(45) Date of Patent: Dec. 8, 2020

(54) COMPOSITIONS AND METHODS FOR TREATING AND PREVENTING CHRONIC PAIN

(71) Applicant: ARIZONA BOARD OF REGENTS ON BEHALF OF THE UNIVERSITY OF ARIZONA, Tucson, AZ (US)

(72) Inventors: Mohab M. Ibrahim, Tucson, AZ (US); Rajesh Khanna, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 121 days.

(21) Appl. No.: 16/306,797

(22) PCT Filed: Jun. 2, 2017

(86) PCT No.: PCT/US2017/035577
§ 371 (c)(1),
(2) Date: Dec. 3, 2018

(87) PCT Pub. No.: WO2017/210498
PCT Pub. Date: Dec. 7, 2017

(65) Prior Publication Data
US 2019/0160304 A1    May 30, 2019

Related U.S. Application Data

(60) Provisional application No. 62/345,205, filed on Jun. 3, 2016.

(51) Int. Cl.
*A61K 45/06* (2006.01)
*A61N 5/06* (2006.01)
(Continued)

(52) U.S. Cl.
CPC .......... *A61N 5/0622* (2013.01); *A61K 45/06* (2013.01); *A61P 23/00* (2018.01); *A61P 29/00* (2018.01);
(Continued)

(58) Field of Classification Search
CPC .......... A61K 45/06; A61N 2005/0648; A61N 2005/0662; A61N 5/0622; A61P 23/00;
(Continued)

(56) References Cited

U.S. PATENT DOCUMENTS

2008/0139941 A1* 6/2008 Njemanze ............. A61B 8/06
                                                            600/455
2014/0277291 A1    9/2014 Pugh
(Continued)

OTHER PUBLICATIONS

Ahmadi, S, et al., ATP-sensitive Potassium Channels and L-type Calcium Channels are Involved in Morphine-induced Hyperalgesia after Nociceptive Sensitization in Mice. Basic Clin Neurosci. 2014 Summer;5(3):191-8.
(Continued)

*Primary Examiner* — George Manuel
(74) *Attorney, Agent, or Firm* — Perkins Coie LLP

(57) ABSTRACT

Provided herein are compositions and methods for managing and minimizing chronic pain. In particular, provided herein are systems and methods for managing and minimizing chronic pain with light therapy.

20 Claims, 13 Drawing Sheets

(51) Int. Cl.
   A61P 29/00     (2006.01)
   A61P 23/00     (2006.01)
   G02C 7/10      (2006.01)
   G02C 5/00      (2006.01)
(52) U.S. Cl.
   CPC ............... G02C 5/00 (2013.01); G02C 7/104 (2013.01); *A61N 2005/0648* (2013.01); *A61N 2005/0662* (2013.01); *G02C 5/001* (2013.01)
(58) Field of Classification Search
   CPC ........... A61P 29/00; G02C 5/00; G02C 5/001; G02C 7/104
   See application file for complete search history.

(56) References Cited

U.S. PATENT DOCUMENTS

2015/0192800 A1    7/2015  Dirk et al.
2015/0238774 A1    8/2015  Anderson

OTHER PUBLICATIONS

Alford, DP., Opioid Prescribing for Chronic Pain—Achieving the Right Balance through Education. N Engl J Med. Jan. 28, 2016;374(4):301-3.
Andersson, DA, et al., Methylglyoxal evokes pain by stimulating TRPA1. PLoS One. Oct. 22, 2013;8(10):e77986.
Bayer, K, et al., Gabapentin may inhibit synaptic transmission in the mouse spinal cord dorsal horn through a preferential block of P/Q-type Ca2+ channels. Neuropharmacology. Apr. 2004;46(5):743-9.
Blake, H, et al., Prescribing opioid analgesics for chronic non-malignant pain in general practice—a survey of attitudes and practice. Br J Pain. Nov. 2015;9(4):225-32.
Bodnar, RJ, et al., Reversal of stress-induced analgesia by apomorphine, but not by amphetamine. Pharmacol Biochem Behav. Aug. 1980;13(2):171-5.
Bourinet, E, et al., T-type calcium channels in neuropathic pain. Pain. Feb. 2016;157 Suppl 1:S15-22.
Butler, RK, et al. Stress-induced analgesia. Prog Neurobiol. Jul. 2009;88(3):184-202.
Carvalho, CM, et al., Wavelength effect in temporomandibular joint pain: a clinical experience. Lasers Med Sci. Mar. 2010;25(2):229-32.
Chaplan, SR, et al., Role of voltage-dependent calcium channel subtypes in experimental tactile allodynia. J Pharmacol Exp Ther. Jun. 1994;269(3):1117-23.
Cidral-Filho, FJ, et al., Light-emitting diode therapy induces analgesia and decreases spinal cord and sciatic nerve tumour necrosis factor-α levels after sciatic nerve crush in mice. Eur J Pain. Sep. 2013;17(8):1193-204.
Cidral-Filho, FJ, et al., Light-emitting diode therapy induces analgesia in a mouse model of postoperative pain through activation of peripheral opioid receptors and the L-arginine/nitric oxide pathway. Lasers Med Sci. Mar. 2014;29(2):695-702.
Colameco, S, et al., Continuous opioid treatment for chronic noncancer pain: a time for moderation in prescribing. Postgrad Med. Jul. 2009;121(4):61-6.
Damaj, MI, et al., Involvement of calcium and L-type channels in nicotine-induced antinociception. J Pharmacol Exp Ther. Sep. 1993;266(3):1330-8.
Dogrul, A, et al., The role of T-type calcium channels in morphine analgesia, development of antinociceptive tolerance and dependence to morphine, and morphine abstinence syndrome. Life Sci. Jun. 28, 2002;71(6):725-34.
Eastman, CI, et al., Bright light treatment of winter depression: a placebo-controlled trial. Arch Gen Psychiatry. Oct. 1998;55(10):883-9.
Figuerio, MG, et al., Tailored lighting intervention improves measures of sleep, depression, and agitation in persons with Alzheimer's disease and related dementia living in long-term care facilities. Clin Interv Aging. Sep. 12, 2014;9:1527-37.
Golden, RN, et al., The efficacy of light therapy in the treatment of mood disorders: a review and meta-analysis of the evidence. Am J Psychiatry. Apr. 2005;162(4):656-62.
Gomaa, AA., Characteristics of analgesia induced by adenosine triphosphate. Pharmacol Toxicol. Sep. 1987;61(3):199-202.
Hatakeyama, S, et al., Differential nociceptive responses in mice lacking the alpha(1B) subunit of N-type Ca(2+) channels. Neuroreport. Aug. 8, 2001;12(11):2423-7.
Heinke, B, et al., Multiple targets of μ-opioid receptor-mediated presynaptic inhibition at primary afferent Aδ- and C-fibers. J Neurosci. Jan. 26, 2011;31(4):1313-22.
Hough, LB, et al., H3 receptors and pain modulation: peripheral, spinal, and brain interactions. J Pharmacol Exp Ther. Jan. 2011;336(1):30-7.
Hsieh, RL, et al., Short-term therapeutic effects of 890-nanometer light therapy for chronic low back pain: a double-blind randomized placebo-controlled study. Lasers Med Sci. Mar. 2014;29(2):671-9.
Jack, MM, et al., Protection from diabetes-induced peripheral sensory neuropathy—a role for elevated glyoxalase I? Exp Neurol. Mar. 2012;234(1):62-9.
Katz, RJ, et al., Stress induced grooming in the rat—an endorphin mediated syndrome. Neurosci Lett. Jul. 1979;13(2):209-12.
Kerr, LM, et al., Autoradiographic localization of calcium channels with [125I]omega-conotoxin in rat brain. Eur J Pharmacol. Jan. 27, 1988;146(1):181-3.
Leichtfried, V, et al., Short-term effects of bright light therapy in adults with chronic nonspecific back pain: a randomized controlled trial. Pain Med. Dec. 2014;15(12):2003-12.
Terman, G.W., et al., Opioid and nonopioid mechanisms of stress analgesia. Science. May 9, 1980;208(4444):623-5.
Luvisetto, S, et al., Pain sensitivity in mice lacking the Ca(v)2.1alpha1 subunit of P/Q-type Ca2+ channels. Neuroscience. Oct. 27, 2006;142(3):823-32.
Maier, SF. Stressor controllability and stress-induced analgesia. Ann N Y Acad Sci. 1986;467:55-72.
Martenson, ME, et al., A possible neural mechanism for photosensitivity in chronic pain. Pain. Apr. 2016;157(4):868-78.
Martins, DF, et al., Light-emitting diode therapy reduces persistent inflammatory pain: Role of interleukin 10 and antioxidant enzymes. Neuroscience. Jun. 2, 2016;324:485-95.
Matthews, EA, et al., The Cav2.3 calcium channel antagonist SNX-482 reduces dorsal horn neuronal responses in a rat model of chronic neuropathic pain. Eur J Neurosci. Jun. 2007;25(12):3561-9.
M'Dahoma, S, et al., Effect of the T-type channel blocker KYS-05090S in mouse models of acute and neuropathic pain. Pflugers Arch. Feb. 2016;468(2):193-9.
Min, PK, et al., 830 nm light-emitting diode low level light therapy (LED-LLLT) enhances wound healing: a preliminary study. Laser Ther. 2013;22(1):43-9.
Moutal, A, et al., (S)-lacosamide inhibition of CRMP2 phosphorylation reduces postoperative and neuropathic pain behaviors through distinct classes of sensory neurons identified by constellation pharmacology. Pain. Jul. 2016;157(7):1448-63.
Nascimento, FP, et al., Adenosine A1 receptor-dependent antinociception induced by inosine in mice: pharmacological, genetic and biochemical aspects. Mol Neurobiol. 2015;51(3):1368-78.
Niederhofer, H, et al., Bright light treatment as add-on therapy for depression in 28 adolescents: a randomized trial. Prim Care Companion CNS Disord. 2011;13(6).
Pelegrini-Da-Silva, A, et al., Angiotensin III modulates the nociceptive control mediated by the periaqueductal gray matter. Neuroscience. Dec. 15, 2009;164(3):1263-73.
Pereira, TS, et al., Efficacy of red and infrared lasers in treatment of temporomandibular disorders—a double-blind, randomized, parallel clinical trial. Cranio. Jan. 2014;32(1):51-6.
Saegusa, H, et al., Suppression of inflammatory and neuropathic pain symptoms in mice lacking the N-type Ca2+ channel. EMBO J. May 15, 2001;20(10):2349-56.
Shutov, L, et al., The effect of nimodipine on calcium homeostasis and pain sensitivity in diabetic rats. Cell Mol Neurobiol. Oct.-Nov. 2006;26(7-8):1541-57.

(56) References Cited

OTHER PUBLICATIONS

Smith, FL, et al., Calcium modulation of morphine analgesia: role of calcium channels and intracellular pool calcium. J Pharmacol Exp Ther. Jan. 1995;272(1):290-9.
Snutch, TP., Targeting chronic and neuropathic pain: the N-type calcium channel comes of age. NeuroRx. Oct. 2005;2(4):662-70.
Spradley, JM, et al., Effects of acute stressors on itch- and pain-related behaviors in rats. Pain. Sep. 2012;153(9):1890-7.
Takahashi, M, et al., The role of the catecholaminergic mechanism in foot shock (FS) stress- and immobilized-water immersion (IW) stress-induced analgesia in mice. Jpn J Pharmacol. Jun. 1984;35(2):175-9.
Zamponi, GW, et al., Role of voltage-gated calcium channels in ascending pain pathways. Brain Res Rev. Apr. 2009;60(1):84-9.

\* cited by examiner

COMPOSITIONS AND METHODS FOR TREATING AND PREVENTING CHRONIC PAIN

CROSS-REFERENCE TO RELATED APPLICATIONS

This application is a Section 371 U.S. national stage entry of International Patent Application No. PCT/US2017/035577, International Filing Date Jun. 2, 2017 which claims priority to and the benefit of U.S. Provisional Application No. 62/345,205, filed Jun. 3, 2016, which are hereby incorporated by reference in their entireties.

This application claims priority to and the benefit of U.S. Provisional Application No. 62/345,205, filed Jun. 3, 2016, which is hereby incorporated by reference in its entirety.

FIELD

Provided herein are compositions and methods for managing and minimizing chronic pain. In particular, provided herein are systems and methods for managing and minimizing chronic pain with light therapy.

BACKGROUND

In the USA, over 100 million patients suffer from chronic pain (see, e.g., Institute of Medicine (U.S.). Committee on Advancing Pain Research Care and Education. Relieving pain in America: a blueprint for transforming prevention, care, education, and research. Washington, D.C.: National Academies Press, 2011). On average, 261-300 billion US dollars are spent annually to manage pain and 297-336 billion US dollars are lost to work productivity. Additionally, the emotional tax from chronic pain has resulted in life altering events ranging from shattering family unity (see, e.g., Smith A A, et al., Journal of advanced nursing 1999; 30(3):543-551) to suicide attempts (see, e.g., Gray, et al., Suicide & life-threatening behavior 2014; 44(3):304-316; Hassett A L, et al., Current pain and headache reports 2014; 18(8):436; Hooley J M, et al., Current pain and headache reports 2014; 18(8):435).

While opioids are the gold standard to treat chronic pain (see, e.g., Hassett A L, et al., Current pain and headache reports 2014; 18(8):436), they are encumbered with side effects (see, e.g., Gray, et al., Suicide & life-threatening behavior 2014; 44(3):304-316). Other medications are utilized for chronic pain such as NSAIDs, antidepressants, anticonvulsants, gabapentoids, and cannabinoids but with limited benefits. The escalating influx of patients with chronic pain combined with patients' expectations for opioids has led to an epidemic of opioid related increase in mortality and morbidity. Sadly, the non-opioid options are limited.

Therefore, non-opioid or non-pharmacological approaches are desperately needed.

SUMMARY

Managing chronic pain is challenging. Opioids are commonly prescribed for chronic pain despite weak evidence for long-term efficacy. The Centers for Disease Control and Prevention recommend non-opioid therapy for chronic pain. While some evidence points to light therapy being beneficial in certain medical conditions, this approach remains to be explored for chronic pain. Provided herein are experiments that describe the antinociceptive effects of several light emitting diodes (LED), in the visible spectrum on naïve and neuropathic pain rats. Daily green LED (wavelength 525 nanometers) exposure for eight hours increased withdrawal latency to noxious thermal stimulus, which persisted for four days following termination of exposure. The antinociception was mediated via actions on central mu-opioid receptor and cannabinoid receptor 1 pathways but did not invoke a stress response or impair motor performance. Blocking pain-facilitation pathways in rostral ventromedial medulla prevented expression of antinociception. The prevention of antinociception with opaque contacts despite LED exposure, occurrence in rats wearing green contacts exposed to room light, or in rats with pigmentation argue for a role of the visual system. Pharmacological and proteomic profiling of dorsal root ganglion (DRG) neurons from green-light exposed rats identified changes in calcium channel activity, including a decrease in the N-type (CaV2.2) channel, a primary analgesic target. Tetrodotoxin-sensitive and -insensitive sodium currents in DRGs were unchanged by green-light exposure. Finally, green-LED exposure reversed thermal and mechanical hyperalgesia in rats with spinal nerve ligation or injection of envelope glycoprotein 120 of HIV-1. Thus, green-LED therapy represents a novel, non-pharmacological approach for managing chronic pain.

Accordingly, provided herein are compositions and methods for treating and preventing chronic pain. In particular, provided herein are systems and methods for treating chronic pain with light therapy.

For example, in some embodiments, the present disclosure provides a method of treating pain, comprising: administering a blue or green spectrum light to the retina of a subject exhibiting pain under conditions such that the subject's pain is reduced or eliminated.

The blue or green spectrum light is not limited to a specific wavelength. In some embodiments, the wavelength is between approximately 450-570 nm. In some embodiments, the wavelength is of 450-495 or 520-560 nm (e.g., 535 nm).

In some embodiments, the administration comprises contacting the eye of the subject with a material that allows light between approximately 450-570 nm to enter the retina of said subject (e.g., contact lens, eye glasses, goggles, ski goggles, or a material that filters polluting light of a wavelength not approximately 450-570 nm) and exposing the subject to broad spectrum light (e.g., via a light box or ambient light). In some embodiments, the subject is contacted with a light source that only emits light of a wavelength of 450-495 or 520-560 nm (e.g., light box).

In some embodiments, the administering is administering light of 4 to 1000 lux (e.g., 4, 12, 46, 110, 330, 500 or 1000 lux) for a time period of 10 minutes to 8 hours (e.g., 10 minutes, 20 minutes, 1, 2, 3, 4, 5, 6, 7, or 8 hours, or fractions thereof) per day. In some embodiments, the administering is administering light of 4 lux for 8 hours per day. In some embodiments, the administering is 20 minutes to 3 hours per day. In some embodiments, the administering is performed for a time period of 3 to 7 days (e.g., 3, 4, 5, 6, or 7 days) or longer. In some embodiments, the administering is 1 hour per day for 3 days. In some embodiments, the administering is repeated after a gap in time or is continuous.

In some embodiments, the pain is any type of pain. In some embodiments, the pain is chronic pain. In some embodiments, the pain is neuropathic pain or chronic myalgia.

In some embodiments, the administering results in release of endogenous opioids and cannabinoids (e.g., endorphins, enkephalins, dynorphins, and/or endomorphins). In some embodiments, the administering results in a biological outcome selected from, for example, one or more of alteration of depolarization-induced $Ca^{2+}$ influx in neurons, alteration of gene expression, or alteration of mu-opioid receptor and cannabinoid receptor I pathways. In some embodiments, the reduction or reversal of pain persists for at least 4 days (e.g., 4, 5, or 6 days, 1, 2, or 3 weeks or 1, 2, 3, 4, 5, or 6 months or longer) after the administration is terminated. In some embodiments, subjects are further administered opioid or non-opioid pain medications (e.g., at lower than typical doses).

Further embodiments provide a kit or system, comprising: a) a light box; and b) an opioid or non-opioid pain management medication. In some embodiments, the light box is configured to emit light between approximately 450-570 nm. In some embodiments, the medication is provided at a reduced dose. Examples of opioid medications include, but are not limited to, hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fentanyl, pethidine, Oxycodone, Oxymorphone, methadone, tramadol, Butorphanol, Levorphanol, or propoxyphene.

Additional embodiments are provided herein.

DESCRIPTION OF THE DRAWINGS

For any colors described in relation to the drawings, the colors have been gray-scaled.

DEFINITIONS

Figure 1:
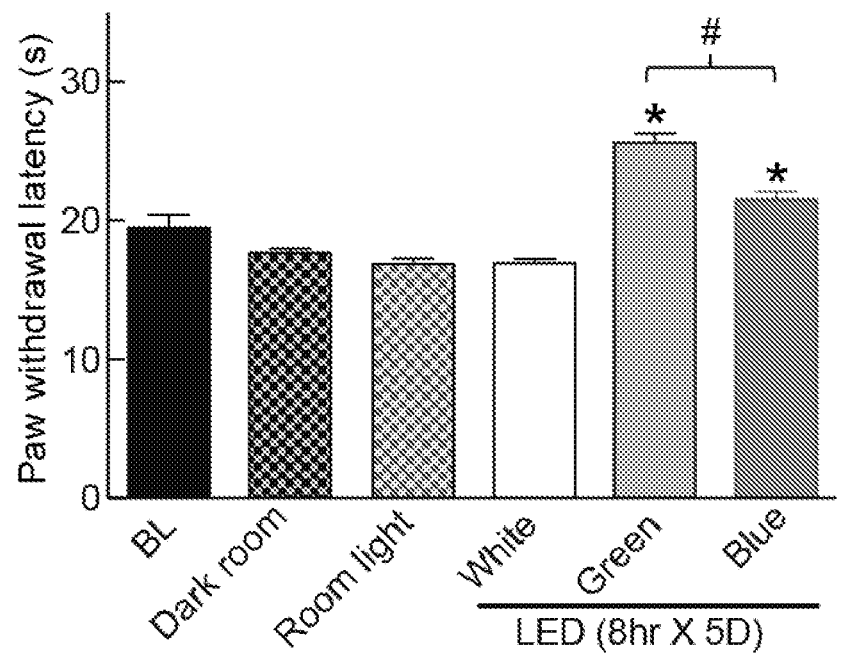
FIG. 1. Effect of light emitting diode (LED) exposure on thermal analgesia in naïve rats. Following measurement of baseline (BL) paw withdrawal latency (PWL, seconds), rats were randomly assigned (n=6 per group) to exposures of eight hours daily for five days to: dark; ambient room light; or white, green ($\lambda$=525 nm) or blue ($\lambda$=472 nm) LED. At the end of this exposure paradigm, PWLs were again measured. Blue and green LED exposure resulted in thermal analgesia. *$p<0.05$ when comparing to white LED (one-way ANOVA followed by Student-Newman-Keuls test) and #$p<0.05$ when comparing between green and blue LED exposures (non-parametric Student's t-test). Unless otherwise stated, the data represent mean±SEM for all figures described herein.

"Energized" as used herein refers to the state of being able to supply electrical current to or to have electrical energy stored within.

"Energy" as used herein refers to the capacity of a physical system to do work.

"Light Source" as used herein refers to a device capable of emitting light.

"Light therapy" as used herein refers to exposure to specific wavelengths of light, controlled with various devices, and administered for a specified amount of time, at a specified intensity and, in some cases, at a specified time of day.

"Lux" as used herein refers to units of illumination in the International System of Units (SI). Lux provides a measure of luminous power per area. One lux is the amount of illumination provided when one lumen is evenly distributed over an area of one square meter. This is also equivalent to the illumination that would exist on a surface from all points of which are one meter from a point source of one international candle. One lux is equal to 0.0929 foot-candle.

"Power" as used herein refers to work done or energy transferred per unit of time.

DETAILED DESCRIPTION

Light therapy has been reportedly effective for certain medical conditions. For example, light therapy, tailored to increase daytime circadian stimulation, improved sleep quality and mitigated depression in Alzheimer's disease (see, e.g., Figueiro M G, et al., Clinical interventions in aging 2014; 9:1527-1537). Additionally, bright light improved the mood of adolescents taking antidepressants compared to those without light therapy (see, e.g., Niederhofer H, et al., Prim Care Companion CNS Disord 2011; 13(6)). Exposing patients to bright light of more than 6000 lux significantly improved seasonal affective disorder (SAD), a serious condition with increased risk of suicidality (see, e.g., Eastman C I, et al., Archives of general psychiatry 1998; 55(10):883-889; Golden R N, et al., The American journal of psychiatry 2005; 162(4):656-662). Finally, exposing patients to light of 830 nanometer wavelength accelerated wound healing (see, e.g., Min P K, et al., Laser therapy 2013; 22(1):43-49).

A randomized clinical trial investigated the effect of bright light exposure in the management of nonspecific back pain where patients received once a week light exposure for 3 weeks reduced pain suggesting an active role for light in controlling pain (see, e.g., Leichtfried V, et al., Pain medicine 2014; 15(12):2003-2012). A double blind randomized placebo-controlled study for chronic low back pain patients exposed to infrared (IR; 890-nanometer wavelength) light experienced significant reduction in fear-avoidance beliefs regarding physical activity and work and severity of disability (see, e.g., Hsieh R L, et al., Lasers in medical science 2014; 29(2):671-679). Two other clinical studies explored the role of red and IR lasers in the management of temporomandibular disorder (TMD) pain. Patients with TMD responded to both red and IR lasers when directed at tender points mapped by palpation over the affected area (see, e.g., Carvalho C M, et al., Lasers Med Sci 2010; 25(2):229-232; Pereira T S, et al., Cranio 2014; 32(1):51-56).

However, light therapy, in particular specific wavelengths of light, for managing pain remains underutilized. Experiments described herein investigated the effect of light as a possible antinociception agent using different wavelengths light emitting diodes (LED) on naïve and neuropathic pain rats. Mechanisms for antinociception were investigated using pharmacological blockers in vivo and constellation pharmacology and whole-cell electrophysiology in vitro.

Experiments showed that in naïve rats, the analgesic-like effects of this phototherapy involves (1) mu-opioid receptor and Cannabinoid Receptor 1 pathways, (2) the visual system, (3) changes in activities of voltage-gated calcium channels, and (4) alterations in the proteome. Green LED phototherapy's ability to reverse reduced nociceptive thresholds in models of neuropathic pain was further demonstrated, supporting its use as a non-pharmacological approach in the treatment of chronic pain.

The complex etiology of neuropathic pain has hindered development of novel therapeutics, forcing physicians to resort to prescribing opioids to manage pain refractory to all available analgesics. While opioids may be necessary for surgical pain or as a palliative measure for patients with terminal and painful conditions, their use in chronic non-malignant conditions is contentious (see, e.g., Alford D P., N Engl J Med 2016; 374(4):301-303; Blake H, et al., Br J Pain 2015; 9(4):225-232; Colameco S, et al., Postgrad Med 2009; 121(4):61-66). Phototherapy has recently emerged as a promising alternative with studies demonstrating light exposure, at 890 or 950 nm wavelengths (i.e., infrared spectrum), promotes analgesia in mouse models of acute (see, e.g., Cidral-Filho F J, et al., Lasers Med Sci 2014; 29(2):695-702), inflammatory (see, e.g., Martins D F, et al., Neuroscience 2016; 324:485-495), and neuropathic pain (see, e.g., Cidral-Filho F J, et al., Eur J Pain 2013; 17(8):1193-1204). Light therapy has been used successfully to manage clinical depression (see, e.g., Niederhofer H, et al., Prim Care Companion CNS Disord 2011; 13(6)) as well as tempomandibular pain (see, e.g., Pereira T S, et al., Cranio 2014; 32(1):51-56; Carvalho C M, et al., Lasers Med Sci 2010; 25(2):229-232). These findings were extended by demonstrating that green light (i.e., 525 nm wavelength) exposure induces antinociception in naïve rats and reverses thermal hyperalgesia and mechanical allodynia associated with two models of neuropathic pain in rats.

A key issue in interpreting photically-induced antinociception is delineation of the route of entry of the light and its connection to a pain modulatory circuit. The observations that all of the green LED-induced antinociception is regulated by access of this wavelength via the visual system and independent of the skin pigmentation argues for a prominent role played by the visual system in the development of antinociception. As to the pain modulatory circuit involved, a study by Heinricher and colleagues (see, e.g., Martenson M E, et al., Pain 2016; 157(4):868-878) identified a possible circuitry for photic stimulation that included pain modulating "ON-cells" and "OFF-cells" in the rostral ventromedial medulla (RVM) which project to the dorsal horn of the spinal cord where they are postulated to modulate somatosensory processing. An imbalance of these can lead to enhanced or diminished pain with ON-cells facilitating nociception and OFF-cells inhibiting nociception.

In experiments described herein, it was demonstrated that green LED-induced antinociception engages central mu-opioid receptors (MORs) as well as cannabinoid receptor 1 (CB1). Suppression of green LED-induced antinociception with the MOR antagonist naloxone, administered systemically, supports a role of peripheral opioid receptors, which is consistent with previous reports demonstrating that administration of naloxone prevents LED therapy induced antinociception in models of post-operative (see, e.g., Cidral-Filho F J, et al., Lasers Med Sci 2014; 29(2):695-702) or inflammatory pain (see, e.g., Martins D F, et al., Neuroscience 2016; 324:485-495). However, the ability of a small dose (20 µg) of naloxone given intrathecally to reverse the antinociception effect argues in favor of a central site of action for the green LED because such a small dose would not be expected to have significant effect if the site of action was in the periphery. Overall, the antinociception may be due to circulating levels of β-endorphin or cannabinoids.

Sensory neuronal sensitization, due to changes in activities of voltage-gated calcium and/or sodium channels, helps to explain the molecular mechanisms underlying green LED-induced antinociception. The overall functional competence, as assessed by their ability to respond to agonists of various receptors, was not different between sensory neurons from rats exposed to ambient light or green LED. However, two notable exceptions included an increased depolarization-induced $Ca^{2+}$ influx in ATP-sensitive neurons as well as an increased $Ca^{2+}$ influx triggered by histamine application of sensory neurons prepared from green light exposed rats. ATP has been directly linked to analgesia (see, e.g., Gomaa A A., Pharmacol Toxicol 1987; 61(3):199-202) while histamine signals through G protein coupled histamine 3 receptors, which have been linked related to antinociception (see, e.g., Hough L B, et al., The Journal of pharmacology and experimental therapeutics 2011; 336(1):30-37), thus both ATP and histamine may underlie the green LED-induced antinociception effect. Consistent with a neuronal sensitization hypothesis involving changes in channel activities, an increase of the depolarization-induced $Ca^{2+}$ influx was observed in sensory neurons prepared from green light exposed rats, shows a greater activity of the voltage-gated $Ca^{2+}$ channels. While most voltage-gated $Ca^{2+}$ channels have been directly linked to pain (i.e., P/Q-type (see, e.g., Luvisetto S, et al., Neuroscience 2006; 142(3):823-832), N-type (see, e.g., Hatakeyama S, et al., Neuroreport 2001; 12(11):2423-2427), R-type (see, e.g., Matthews E A, et al., The European journal of neuroscience 2007; 25(12):3561-3569) and T-type (see, e.g., Bourinet E, et al., Pain 2016; 157 Suppl 1:S15-22)), the L-type voltage-gated $Ca^{2+}$ channels activity have been shown to not contribute to nociception (see, e.g., Chaplan S R, et al., The Journal of pharmacology and experimental therapeutics 1994; 269(3):1117-1123) and has been proposed to participate in the antinociceptive effects of morphine (see, e.g., Ahmadi S, et al., Basic Clin Neurosci 2014; 5(3):191-198) or nicotine (see, e.g., Damaj M I, et al., The Journal of pharmacology and experimental therapeutics 1993; 266(3):1330-1338). In investigating the exact calcium channel subtype(s) responsible for the global increase in depolarization-induced calcium influx, it was found that the L-, P/Q-, and T-type channels to have increased activity in sensory neurons while the N-type (CaV2.2) channel was partially inhibited. CaV2.2 is believed to be responsible for increased neurotransmitter release (e.g., calcitonin gene related peptide (CGRP)) commonly associated with chronic and neuropathic pain conditions (see, e.g., Kerr L M, et al., EurJPharmacol 1988; 146(1):181-183; Snutch T P., NeuroRx 2005; 2(4):662-670; Zamponi G W, et al., Brain research reviews 2009; 60(1): 84-89). Consistent with the role of CaV2.2 in pain signaling, genetic deletion, as well as pharmacologic block of CaV2.2, impairs nociceptive processing (see, e.g., Saegusa H, et al., EMBO J 2001; 20(10):2349-2356; Maier S F., Ann N Y Acad Sci 1986; 467:55-72). The N-type calcium channel is the primary target of morphine-induced analgesia through a G-protein coupled receptor mechanism (see, e.g., Heinke B, et al., The Journal of neuroscience : the official journal of the Society for Neuroscience 2011; 31(4):1313-1322). Moreover, direct (Prialt) and indirect (gabapentin) inhibitors of CaV2.2 are FDA-approved drugs for the management of chronic pain. Inhibition of L-, P/Q-, and T-type calcium channels has also been reported to achieve pain-relief (see, e.g., Bayer K, et al., Neuropharmacology 2004; 46(5):743-749; Luvisetto S, et al., Neuroscience 2006; 142(3):823-832; M'Dahoma S, et al., Pflugers Arch 2016; 468(2):193-199; Shutov L, et al., Cell Mol Neurobiol 2006; 26(7-8):1541-1557). The increased activity of these three channel subtypes appears to be contradictory with the antinociception produced by the green light treatment. Although the precise mechanisms remain unknown, activity of the L-, P/Q-, or T-type calcium channels was found to be required for MOR-dependent pain-relief (see, e.g., Smith F L, et al., J Pharmacol Exp Ther 1995; 272(1):290-299; Dogrul A, et al., Life Sci 2002; 71(6):725-734; Ahmadi S, et al., Basic Clin Neurosci 2014; 5(3):191-198). Thus, it was contemplated that the green light treatment could increase the activity of these channels as part of the mechanism of antinociception commensurate with an increased activation of MORs. Finally, no changes were observed in sodium channels ruling out their involvement in neuronal sensitization and green LED-induced analgesia.

An unbiased proteomics approach identified a protein signature in dorsal root ganglia and dorsal horn of green LED exposed antinociceptive rats. Stratification of proteins based on gene ontology (GO) terms corresponding to the biological processes, molecular functions, and cellular components revealed an enrichment of proteins related to "antioxidant activity" in the ganglia of green LED exposed rats, a finding consistent with the reported reduction in antioxidant activities (e.g., catalase and superoxide dismutase) in rats with inflammatory pain (see, e.g., Martins D F, et al., Neuroscience 2016; 324:485-495). A reduction in the number of membrane-localized proteins in dorsal horn green LED exposed rats was also observed, which likely correlates with decreased signaling capabilities of neurons. The findings also uncovered proteins enriched in tissues from green LED exposed rats that have are reported to be linked to antinociception (Table 2). For example, the enzyme purine nucleoside phosphorylase breaks down adenosine into inosine, which has antinociceptive properties via actions on the Adenosine A1 receptor (see, e.g., Nascimento F P, et al., Mol Neurobiol 2015; 51(3):1368-1378). This is entirely consistent with the findings, from constellation pharmacology experiments, which demonstrated a decrease in ATP sensitive neurons. Another enzyme, aspartyl aminopeptidase, which converts angiotensin II to angiotensin III, has been reported to activate inhibitory pain descending pathways from the periaqueductal gray matter (see, e.g., Pelegrini-da-Silva A, et al., Neuroscience 2009; 164(3):1263-1273). The findings on chemical inactivation of the RVM further support a role of inhibitory pain descending pathways in green LED mediated antinociception. Yet another example is the enzyme lactoylglutathione lyase (i.e., glyoxalase-1), which catalyzes the detoxification of methylglyoxal, a cytotoxic ketoaldehyde, which is directly linked to activating nociceptors (see, e.g., Andersson D A, et al., PloS one 2013; 8(10):e77986). Moreover, expression of glyoxalase-1 is reduced in diabetic neuropathy (see, e.g., Jack M M, et al., Experimental neurology 2012; 234(1):62-69). These lines of evidence, along with those listed in Table 2, build a picture consistent with global changes induced by green LED to produce antinociception.

TABLE 2

| Identified proteins | Gene Name | Accession number[1] | % sequence coverage | Pain implication |
|---|---|---|---|---|
| DRG | | | | |
| Carboxypeptidase | ctsa | Q6AYS3_RAT | 12% | Enkephalin degradation (see, e.g., Chipkin R E, et al., European journal of pharmacology 1982; 83(3-4):283-288) |
| Alpha-synuclein | snca | SYUA_RAT | 46% | Expressed in laminae I, II, VII and X of the dorsal horn (see, e.g., Vivacqua G, et al., Neuroscience 2009; 158(4):1478-1487) |
| Microtubule-associated protein | mapt | F1LST4_RAT | 19% | Lost in neuropathic pain (see, e.g., Kim D S, et al., Neuroreport 2001; 12(15):3401-3405) |
| Thioredoxin | txn | THIO_RAT | 54% | Improves ziconotide induced analgesia [88] Expression is changed after surgery (see, e.g., Fricova J, et al., Arch Med Sci 2010; 6(5):764-771) |
| Stathmin | stmn1 | STMN1_RAT | 37% | Substrate for Cdk5 (see, e.g., Shah K, Lahiri D K. A Tale of the Good and Bad: Remodeling of the Microtubule Network in the Brain by Cdk5. Mol Neurobiol 2016) |
| Acid ceramidase | asah1 | A0A0G2K8T0_RAT | 28% | Inactivating mutation in Farber disease (patients experience pain) (see, e.g., Zhou J, et al., Am J Hum Genet 2012; 91(1):5-14; Bonafe L, Kariminejad A, Li J, Royer-Bertrand B, Garcia V, Mandavi S, Bozorgmehr B, Lachman R L, Mittaz-Crettol L, Campos-Xavier B, Nampoothiri S, Unger S, Rivolta C, Levade T, Superti-Furga A. Peripheral osteolysis in adults linked to ASAH1 (acid ceramidase) mutations: A new presentation of Farber disease. Arthritis Rheumatol 2016) |
| Haptoglobin | hp | A0A0H2UHM3_RAT | 18% | Serum concentration decreased in abdominal pain in horses (see, e.g., Pihl T H, et al., Vet Clin Pathol 2013; 42(2):177-183) |
| Cofilin 2 | cfl2 | M0RC65_RAT | 46% | Phosphorylation is associated with hyperalgesia (see, e.g., Li Y, et al., Sci Signal 2014; 7(331):ra61; Zulauf L, et al., Biochemical and biophysical research communications 2009; 390(4):1408-1413) |
| Calretinin | calb2 | CALB2_RAT | 21% | Protects against TRPV1-mediated toxicity in pain-sensing neurons (see, e.g., Pecze L, et al., Biochimica et biophysica acta 2013; 1833(7):1680-1691) |
| Lactoylglutathione lyase | glo1 | LGUL_RAT | 45% | Expression reduced in diabetic neuropathy (see, e.g., Jack M M, et al., Experimental neurology 2012; 234(1):62-69) catalyses the detoxification of Methylglyoxal, a positive regulator of TRPA1, unregulated during painful neuropathy (see, e.g., Andersson D A, et al., PloS one 2013; 8(10):e77986) |

TABLE 2-continued

| Identified proteins | Gene Name | Accession number[1] | % sequence coverage | Pain implication |
|---|---|---|---|---|
| DH | | | | |
| Lactoylglutathione lyase | glol | LGUL_RAT | 54% | Expression reduced in diabetic neuropathy (see, e.g., Jack M M, et al., Experimental neurology 2012; 234(1):62-69) catalyses the detoxification of Methylglyoxal, a positive regulator of TRPAI, upregulated during painful neuropathy (see, e.g., Andersson D A, et al., PloS one 2013; 8(10):e77986) |
| Purine nucleoside phosphorylase | pnp | PNPH_RAT | 25% | Catalyses the breakdown of adenosine into inosine, which induces anti-nociception in the formalin test (see, e.g., Nascimento F P, et al., Mol Neurobiol 2015; 51(3):1368-1378) |
| Aspartyl aminopeptidase | dnpep | Q4V8H5_RAT | 17% | Catalyses angiotensin III synthesis which activates inhibitory pain descending pathways from the periaqueductal gray matter (see, e.g., Pelegrini-da-Silva A, et al., Neuroscience 2009; 164(3):1263-1273) |
| Cathepsin B | ctsb | Q6IN22_RAT | 22% | Expressed in microglia during inflammatory pain (see, e.g., Sun L, et al., The Journal of neuroscience: the official journal of the Society for Neuroscience 2012; 32(33):11330-11342) |
| Alpha glucosidase 2 alpha neutral subunit | ganab | D3ZAN3_RAT | 14% | Deficiency causes Pompe disease with increased mild pain (see, e.g., Gungor D, et al., Mol Genet Metab 2013; 109(4):371-376) |

Overall, experiments described herein identified the cellular and molecular basis of green LED-mediated antinociception. From a translational perspective, the discovery that green LED exposure is antinociceptive in naïve animals and can reverse established pain in others, opens up routes for the development of phototherapy as a non-invasive, non-pharmacological therapeutic approach for pain. Consequently, modulating the duration and intensity of green LED should also prove useful in the clinic for reducing opioid consumption for pain management.

Accordingly, provided herein is a method of treating pain, comprising: administering a blue or green spectrum light to the retina of a subject exhibiting pain under conditions such that the subject's pain is reduced or eliminated.

The blue or green spectrum light is not limited to a specific wavelength. In some embodiments, the wavelength is between approximately 450-570 nm. In some embodiments, the wavelength is of 450-495 or 520-560 nm (e.g., 535 nm).

In some embodiments, the administration comprises contacting the eye of the subject with a material that allows light between approximately 450-570 nm to enter the retina of said subject (e.g., contact lens, eye glasses, goggles, ski goggles, or a material that filters polluting light of a wavelength not approximately 450-570 nm) and exposing the subject to broad spectrum light (e.g., via a light box or ambient light). In some embodiments, the subject is contacted with a light source that only emits light of a wavelength of 450-495 or 520-560 nm (e.g., light box).

In some embodiments, light of 4 to 1000 lux (e.g., 4, 12, 46, 110, 330, 500 or 1000 lux) is administered for a time period of 10 minutes to 8 hours (e.g., 10 minutes, 20 minutes, 1, 2, 3, 4, 5, 6, 7, or 8 hours, or fractions thereof) per day. In some embodiments, the administering is administering light of 4 lux for 8 hours per day. In some embodiments, the administering is 20 minutes to 3 hours per day. In some embodiments, the administering is performed for a time period of 3 to 7 days (e.g., 3, 4, 5, 6, or 7 days) or longer. In some embodiments, the administering is 1 hour per day for 3 days.

In some embodiments, the administering is repeated after a gap in time or is continuous. The present invention is not limited to treatment of particular types of pain. In some embodiments, the pain is chronic pain. In some embodiments, the pain is neuropathic pain or chronic myalgia. In some embodiments, the administering results in release of endogenous opioids and cannabinoids (e.g., endorphins, enkephalins, dynorphins, and/or endomorphins). In some embodiments, the administering results in a biological outcome selected from, for example, one or more of alteration of depolarization-induced $Ca^{2+}$ influx in neurons, alteration of gene expression, or alteration of mu-opioid receptor and cannabinoid receptor I pathways. In some embodiments, the reduction or reversal of pain persists for at least 4 days (e.g., 4, 5, or 6 days, 1, 2, or 3 weeks or 1, 2, 3, 4, 5, or 6 months or longer) after the administration is terminated. In some embodiments, subjects are further administered opioid medications (e.g., at lower than typical doses).

In some embodiments, the luminaire includes an autonomous clock so that the luminaire may emit the prescribed output spectra at an indicated time of day. Therefore, if a patient prefers to use a luminaire at a particular time of day, the luminaire may be programmed to automatically emit the prescribed output spectra at that time. As a result, the patient will not have to worry about switching the luminaire on or off when they would typically prefer to utilize the luminaire. In some embodiments, the autonomous clock may be an atomic clock.

In some embodiments, light boxes utilize a LED light source based upon existing technology such as the high-powered LED light available from Diamond Marketing Ltd. More recent LED light sources may also be used.

Light emitting diodes are known which, when disposed on a circuit, accept electrical impulses from the circuit and convert the impulses into light signals. LEDs are energy efficient, they give off virtually no heat, and they have a long lifetime.

A number of types of LED exist, including air gap LEDs, GaAs light-emitting diodes (which may be doubled and packaged as single unit offer greater reliability than conventional single-diode package), polymer LEDs, and semiconductor LEDs, among others. Most LEDs in current use are red. Conventional uses for LEDs include displays for low light environments, such as the flashing light on a modem or other computer component, or the digital display of a wristwatch. Improved LEDs have recently been used in arrays for longer-lasting traffic lights. LEDs have been used in scoreboards and other displays. Also, LEDs have been placed in arrays and used as television displays. Although most LEDs in use are red, yellow or white, LEDs may take any color; moreover, a single LED may be designed to change colors to any color in the color spectrum in response to changing electrical signals.

Computer lighting networks that use LEDs are also known. U.S. Pat. No. 5,420,482, issued to Phares, describes one such network that uses different colored LEDs to generate a selectable color, primarily for use in a display apparatus. U.S. Pat. No. 4,845,481, issued to Havel, is directed to a multicolored display device. Havel uses a pulse width modulated signal to provide current to respective LEDs at a particular duty cycle. U.S. Pat. No. 5,184,114, issued to Brown, shows an LED display system. U.S. Pat. No. 5,134,387, issued to Smith et al., is directed to an LED matrix display.

In some embodiments, the present invention provides a kit or system, comprising: a light box or luminaire or material that only allow light of a pre-determined wavelength to enter the eye (e.g., lenses and eyewear described herein); and an opioid medication. In some embodiments, the light box is configured to emit light between approximately 450-570 nm. In some embodiments, the opioid medication is provided at a reduced dose.

The methods described herein find use in the treatment of a variety of types of pain. In some embodiments, the pain is chronic pain. In some embodiments, the pain is neuropathic pain. In some embodiments, the administering results in release of endogenous opioids and cannabinoids. In some embodiments, the reduction or reversal of pain persists for at least 4 days (e.g., 4, 5, or 6 days, 1, 2, or 3 weeks or 1, 2, 3, 4, 5, or 6 months or longer) after the administration is terminated. In some embodiments, treatment is repeated as needed to reduce or eliminate pain. In some embodiments, subjects are further administered opioid medications (e.g., at lower than typical doses).

In some embodiments, methods and compositions described herein are utilized in combination with opioid and non-opioid pain relieving agents. In some embodiments, the pain relieving agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Examples of analgesics include, but are not limited to, tricyclic antidepressants (e.g., amitriptyline, carbamazepine, gabapentin, and pregabalin), Tetrahydrocannabinol, ketamine, clonidine, $\alpha_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain relieving agents include anesthetic drugs. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (Amytal), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Etomidate, Ketamine, Propofol).

In some embodiments, pain relieving agents include anticonvulsant drugs. Examples of anticonvulsant drugs include, but are not limited to, aldehydes (e.g., paraldehyde), aromatic allylic alcohols (e.g., stiripentol), barbiturates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain relieving agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

EXPERIMENTAL

Example 1

Methods
Animals

Pathogen-free, adult male and female Sprague-Dawley as well as male Long Evans rats (weight at testing 250-350 g; Harlan-Sprague-Dawley, Indianapolis, Ind.) were housed in a climate-controlled room on a 12-h light/dark cycle and were allowed to have food and water ad libitum. All procedures were approved by the University of Arizona Animal Care and Use Committee and conform to the guidelines for the use of laboratory animals of the National Institutes of Health (publication no. 80-23, 1966). All behavioral experiments were conducted by experimenters blinded to the treatment conditions.

Chemicals

All experimental compounds, doses, sources, and catalog numbers are described in Table 1. The viral envelope glycoprotein 120 (gp120) of HIV-1 was obtained from the NIH AIDS Reagent Program (catalog 11784; recombinant HIV-1 IIIB gp120).

TABLE 1

Compounds

| Experimental compound | Vendor | Catalog number | Target/mechanism of action | Dose | Route |
|---|---|---|---|---|---|
| Naloxone | Tocris | 0599 | non-selective opioid receptors | 2 mg/kg | Intraperitoneal (i.p.) |
|  |  |  |  | 20 µg | Intrathecal (i.t.) |
| AM251 | Tocris | 1117 | Cannabinoid receptor 1 (CB1) | 1 mg/kg | i.p. |
| AM630 | Tocris | 1120 | Cannabinoid receptor 2 (CB2) | 1 mg/kg | i.p. |
| Phentolamine | Sigma | P7547 | beta-adrenergic receptor | 3 mg/kg | i.p. |
| Propranolol | Sigma | P0884 | beta1-/beta2-adrenergic receptor | 10 mg/kg | i.p. |
| Phenoxybenzamine | Sigma | B019 | alpha 1-adrenergic receptor | 1 mg/kg | i.p. |

Light Emitting Diodes (LED).

All visible spectrum LED flex strips were purchased from ledsupply.com (VT, USA). The specification of the LED were: (i) #LS-AC60-6-BL, 472 nanometer wavelength (i.e., blue), 8 watts, 120 Volts, 120 degree beam angle; (ii) #LS-AC60-6-GR, 525 nanometer wavelength (i.e., green), 8 watts, 120 Volts, 120 degree beam angle; and (iii) #LS-AC60-66-WH, white, 9.6 watts, 120 Volts, 120 degree beam angle. LED strips were affixed to the outside of clear plastic cages that housed the rats so as to avoid the strips from being chewed. Rats were exposed to the various LED in these cages with full access to food and water in a dark room devoid of any other source of light. Following behavioral assessment, the rats were returned to their cages for additional LED exposure. At the end of daily testing, the rats were returned to their regular animal room where they were exposed to regular room light (regular florescent bulbs). A lux meter (Tondaj LX1010B, Amazon.com) was used to determine the illuminance and luminous emittance of the LED strips.

Measurement of Thermal Withdrawal Latency

The method of Hargreaves et al. (see, e.g., Hargreaves K, et al., Pain 1988; 32(1):77-88) was used. Rats were acclimated within Plexiglas enclosures on a clear glass plate maintained at 30° C. A radiant heat source (high-intensity projector lamp) was focused onto the plantar surface of the hind paw. When the paw was withdrawn, a motion detector halted the stimulus and a timer. A maximal cutoff of 33.5 sec was used to prevent tissue damage.

Testing of Allodynia.

The assessment of tactile allodynia (i.e., a decreased threshold to paw withdrawal after probing with normally innocuous mechanical stimuli) consisted of testing the withdrawal threshold of the paw in response to probing with a series of calibrated fine (von Frey) filaments. Each filament was applied perpendicularly to the plantar surface of the paw of rats held in suspended wire mesh cages. Withdrawal threshold was determined by sequentially increasing and decreasing the stimulus strength (the "up and down" method), and data were analyzed with the nonparametric method of Dixon (see, e.g., Chaplan S R, et al., Journal of neuroscience methods 1994; 53(1):55-63) and expressed as the mean withdrawal threshold.

Implantation of Intrathecal Catheter.

For intrathecal drug administration, rats were chronically implanted with catheters (see, e.g., Yaksh T L, et al., Physiology & behavior 1976; 17(6):1031-1036). Rats were anesthetized with isoflurane and placed in a stereotactic device. The occipital muscles were separated from their occipital insertion and retracted caudally to expose the cisternal membrane at the base of the skull. Polyethylene tubing was passed caudally from the cisterna magna to the level of the lumbar enlargement. Animals were allowed to recover and were examined for evidence of neurologic injury. Animals with evidence of neuromuscular deficits were excluded.

Fabricating Contact Lens for the Rats and Imaging of Eyes Post-Mortem.

All plastic materials were purchased from Evergreen Scale Models (Des Plaines, Ill.). The method developed by Levinson et al (see, e.g., Sheridan DMLaCL. Bahavior Research Methods & Instrumentation 1978; 10(3):376-388) was used, with the following modifications. In brief, 0.25 mm sheets were cut into 2 $cm^2$ pieces held by forceps over a 6 mm ball bearing, shaped when malleable with a copper pipe of 9 mm internal diameter and then trimmed in to a truncated hemisphere with iris scissors and sanded with a fine grit and emery cloth to a depth of 3.5±0.2 mm and a base diameter of 7.0±0.2 mm. A Wellar 1095-1000 watt dual temperature heat gun was used instead of the Bunsen burner used by Levinson, as a heat source for the fabrication process. The rats where anesthetized using isoflurane just long enough to place the contact lens in their eyes and were allowed to recover from anesthesia. The rats were anesthetized again with isoflurane to remove the contact lens at the end of each 8 hour exposure.

To examine if the contact lens induced any pathological damage, at the end of the experiment, the corneas were excised with the small rim of the sclera and then fixed for 30 minutes with 4% paraformaldehyde in phosphate buffered saline as described previously (see, e.g., Nyberg M A, et al., Albrecht Von Graefes Arch Klin Exp Ophthalmol 1977; 204(3):153-159). Next, the corneas were transferred to 30% sucrose solution until staining with Evans blue solution for 1 min. The Evans blue dye solution was prepared by mixing 1 ml of a commercially prepared 0.5% Evans blue sterile aqueous solution with 9 ml of normal saline. This yielded a final solution of 0.05% Evans blue, with a pH of 6.75. After staining, the excess dye was removed by gently passing the tissue through two baths of normal saline solution. Light microscope images were obtained of the stained corneas on an Olympus BX51 microscope with a Hamamatsu C8484 digital camera using a 4× UplanFL N, 0.13 numerical aperture or a 20× UplanSApo 0.75 numerical aperture objective. The freeware image analysis program Image J (http://rsb.info.nih.gov/ij/) was used to generate merged images.

Spinal Nerve Ligation (SNL).

Nerve ligation injury produces signs of neuropathic dysesthesias, including tactile allodynia and thermal hypersensitivity (see, e.g., Kim K J, et al., Experimentelle Himforschung Experimentation cerebrale 1997; 113(2):200-206). All nerve operations occurred 5 days after intrathecal catheter implantation. Rats were anesthetized with 2% isoflurane in $O_2$ anesthesia delivered at 2 L/min (total time under anesthesia was <60 minutes). The skin over the caudal lumbar region was incised and the muscles retracted. The $L_5$ and $L_6$ spinal nerves were exposed, carefully isolated, and tightly ligated with 4-0 silk distal to the dorsal root ganglion without limiting the use of the left hind paw of the animal. All animals were allowed 7 days to recover before any behavioral testing. Any animals exhibiting signs of motor deficiency were euthanized. Sham control rats underwent the same operation and handling as the SNL animals, but without the nerve ligation.

Rostral Ventromedial Medulla (RVM) Cannulation.

Rats received a bilateral guide cannula (26GA, #C235-1.2 mm, Plastics One Inc.) directed to the RVM. The cannula was placed at: −11.0 from bregma, −7.5 mm from the dura and 0.6 mm on either side of the midline. Injections were made by expelling 0.5 µl through an injection cannula protruding 1 mm beyond the tip of the guide. Cannula placement was confirmed with 0.5 µl Evans Blue injected into both sides of the cannula and microscopic examination of medullary sections. Acute single injections into the RVM were performed by inserting an injector (Plastics One Inc) attached to a 2 µl Hamilton syringe and expelling 0.5 µl at the same coordinates.

HIV Sensor Neuropathy (HIV SN).

Thermal hyperalgesia and mechanical allodynia are produced by intrathecal administration of the human immunodeficiency virus-1 (HIV-1) envelope glycoprotein, gp120 (see, e.g., Milligan E D, et al., The Journal of neuroscience: the official journal of the Society for Neuroscience 2001; 21(8):2808-2819). Seven days after implantation of an intrathecal catheter, baseline behavioral measurements were obtained and then rats were randomly assigned to two groups. On days 10 and 13, one group of rats were injected i.t. with 300 ng gp120 in a final volume of 20 µl in 0.9% saline while the other group were injected in a similar fashion with 0.9% saline.

Rotarod.

Rats were trained to walk on a rotating rod (10 rev/min, Rotamex 4/8 device) with a maximal cutoff time of 180 seconds. Training was initiated by placing the rats on a rotating rod and allowing them to walk on the rotating rod until they either fell off or 180 seconds was reached. This process was repeated 6 times and the rats were allowed to recover for 24 hours before beginning green LED exposure. Prior to treatment, the rats were run once on a moving rod in order to establish a baseline value. Assessment consisted of placing the rats on the moving rod and timing until either they fell off or reached a maximum of 180 seconds.

Immunohistofluorescence and Epifluorescence Imaging.

Dorsal root ganglia (DRG) and lumbar spinal cord were dissected from adult rats and then fixed using 4% paraformaldehyde for 4 hrs at room temperature (RT). TGs were next transferred into a 30% sucrose solution and left at 4° C. until the sinking of the tissues could be observed (~3 days). Tissues were cut at 10 μm thickness using the Bright OTF 5000 Microtome Cryostat (Hacker Instruments and Industries, Inc., Winnsboro, S.C.), and fixed onto gelatin coated glass slides and kept at −20° C. until use. Prior to antibody staining, slides were dried at room temperature for 30 min and incubated with phosphate buffered saline (PBS) containing 200 mM NH$_4$Cl for 30 min. Next, the slides were incubated with PBS containing 3% sodium deoxycholate for 30 min at RT; these two PBS incubations were performed to reduce the background fluorescence of the tissue. TG slices were permeabilized and saturated using PBS containing 3% BSA, 0.3% triton X-100 solution for 30 min at RT, and then antibodies were added overnight. The antibodies used were: CGRP (Cat #C8198, Sigma, St Louis, Mo.); Substance P (Cat #Ab1977, chemicon, Billerica, Mass.). The slices were then washed 3× in PBS, and incubated with PBS containing 3% BSA, 0.3% triton X-100 containing secondary antibodies (Alexa 488 goat anti-rabbit or Alexa 594 goat anti-mouse secondary antibodies (Life Technologies)) for at least 3 hrs at RT. After 3 washes (PBS, 10 min, RT), neurotrace (Cat #N21479, Thermo Fisher Scientific) was used to stain neuronal soma. Slides were mounted and stored at 4° C. until analysis. Immunofluorescent micrographs were acquired on an Olympus BX51 microscope with a Hamamatsu C8484 digital camera using a 4× UplanFL N, 0.13 numerical aperture or a 20× UplanSApo 0.75 numerical aperture objective. The freeware image analysis program Image J (http://rsb.info.nih.gov/ij/) was used to generate merged images.

Primary Dorsal Root Ganglion (DRG) Neuronal Cultures.

Sensory DRG neurons from Sprague-Dawley rats were isolated as described previously (see, e.g., Dustrude E T, et al., The Journal of biological chemistry 2013; 288(34): 24316-24331; Brittain J M, et al., Nature medicine 2011; 17(7):822-829). Dorsal root ganglia (from thoracic 2 to lumbar 6 spinal levels) were excised aseptically and placed in Hank buffered salt solution (HBSS, Life technologies) containing penicillin (100 U/mL) and streptomycin (100 μg/mL, Cat #15140, Life technologies) on ice. The ganglia were dissociated enzymatically by a 45 min incubation (37° C.) in a DMEM (Cat #11965, Life technologies) solution containing neutral protease (3.125 mg·ml$^{-1}$, Cat #LS02104, Worthington) and collagenase Type I (5 mg·ml$^{-1}$, Cat #LS004194, Worthington). The dissociated cells were resuspended in complete DRG medium, DMEM containing penicillin (100 U/mL), streptomycin (100 μg/mL), 30 ng·ml$^{-1}$ nerve growth factor and 10% fetal bovine serum (Hyclone). For Ca$^{2+}$ imaging, the cells were seeded on poly-D-lysine (Cat #P6407, Sigma) coated glass coverslips (Cat #72196-15, electron microscopy sciences) as a drop of 20 μl on the center of each coverslip, then placed in a 37° C., 5% CO$_2$ incubator for 45-60 min to allow cells to attach. Then the cultures were flooded by gently adding complete DRG medium on the edge of each well to avoid detaching any weakly adherent cell.

Calcium Imaging.

DRG neurons were loaded at 37° C. with 3 μM Fura-2AM (Cat #F-1221, Life technologies, stock solution prepared at 1 mM in DMSO, 0.02% pluronic acid, (Cat #P-3000MP, Life technologies) for 30 minutes ($K_d$=25 μM, $\lambda_{ex}$ 340, 380 nm/$\lambda_{emi}$ 512 nm) to follow changes in intracellular calcium ([Ca$^{2+}$]$_c$) in Tyrode's solution (at ~310 mOsm) containing 119 mM NaCl, 2.5 mM KCl, 2 mM MgCl$_2$, 2 mM CaCl$_2$, 25 mM HEPES, pH 7.4 and 30 mM glucose. All calcium-imaging experiments were done at room temperature (~23° C.). Fluorescence imaging was performed with an inverted microscope, Nikon Eclipse Ti-U (Nikon Instruments Inc.), using objective Nikon Super Fluor MTB FLUOR 10× 0.50 and a Photometrics cooled CCD camera CoolSNAP ES$^2$ (Roper Scientific) controlled by NIS Elements software (version 4.20, Nikon instruments). The excitation light was delivered by a Lambda-LS system (Sutter Instruments). The excitation filters (340±5 nm and 380±7 nm) were controlled by a Lambda 10-2 optical filter change (Sutter Instruments). Fluorescence was recorded through a 505 nm dichroic mirror at 535±25 nm. To minimize photobleaching and phototoxicity, the images were taken every 10 seconds during the time-course of the experiment using the minimal exposure time that provided acceptable image quality. The changes in [Ca$^{2+}$]$_c$ were monitored by following the ratio of $F_{340}/F_{380}$, calculated after subtracting the background from both channels.

Pharmacological Profiling of Sensory Neurons.

After a 1-minute baseline measurement, Ca$^{2+}$ influx was stimulated by the addition of the following receptor agonists, in order: 1 mM acetylcholine (Ach), 200 μM allyl isothiocyanate (AITC), 10 μM adenosine triphosphate (ATP), 50 μM histamine, 400 nM menthol and 100 nM capsaicin diluted in Tyrode's solution. At the end of the pharmacological profiling protocol, cell viability was assessed by depolarization-induced Ca$^{2+}$ influx using and an excitatory KCl solution comprised of 32 mM NaCl 90 mM KCl, 2 mM MgCl$_2$, 2 mM CaCl$_2$, 25 mM HEPES, pH 7.4, 30 mM glucose. After the 1-minute baseline measurement, each trigger was applied for 15-seconds in the order indicated above in 2-minutes intervals. Following each trigger, bath solution was continuously perfused over the cells to wash off excess of the trigger and to let the sensory neurons return to baseline. This process was automated using the software WinTask x64 (Version 5.1, WinTask) that controlled the perfusion of the standard bath solution and triggers through Valvelink 8.2 software (Automate Scientific). A cell was defined as a 'responder' if its fluorescence ratio of $F_{340}/F_{380}$ was greater than 10% of the baseline value calculated using the average fluorescence in the 30 seconds preceding application of the trigger.

To isolate each voltage-gated calcium channel (VGCC) subtypes, cells were incubated during the 30 min Fura2-AM loading step with a combination of compounds inhibiting all voltage-gated calcium channels subtype but one. The compounds (all purchased from Alomone labs, Jerusalem, Israel) used were nifedipine (10 μM, L-type), SNX-482 (200 nM, R-type) (see, e.g., Newcomb R, et al., Biochemistry 1998; 37(44):15353-15362), ω-conotoxin GVIA (500 nM, N-type) (see, e.g., Feng Z P, et al., The Journal of biological chemistry 2001; 276(19):15728-15735), ω-agatoxin TK (200 nM, P/Q-type) (see, e.g., Mintz I M, et al., Nature 1992; 355(6363):827-829) and 3,5-dichloro-N-(1-[2,2-dimethyl-tetrahydro-pyran-4-ylmethyl]-4-fluoro-piperidin-4-ylin-ethyl)-benzamide (TTA-P2, 1 μM, T-type) (see, e.g., Choe W, et al., Molecular pharmacology 2011; 80(5):900-910).

Whole-Cell Voltage Clamp Electrophysiology.

Whole cell voltage clamp recordings were performed at room temperature using an EPC 10 Amplifier-HEKA as previously described (see, e.g., Dustrude E T, et al., The Journal of biological chemistry 2013; 288(34):24316-24331). The internal solution for voltage clamp recordings of DRG cells contained (in mM): 140 CsF, 1.1 Cs-EGTA, 10 NaCl, and 15 HEPES (pH 7.3, 290-310 mOsm/L) and the external solution contained (in mM): 140 NaCl, 3 KCl, 30 tetraethylammonium chloride, 1 CaCl$_2$, 0.5 CdCl$_2$, 1 MgCl$_2$, 10 D-glucose, 10 HEPES (pH 7.3, 310-315 mosM/L).

Electrodes were pulled from standard wall borosilicate glass capillaries from Warner Instruments with a P-97 electrode puller from Sutter Instruments and heat polished to final resistances of 1.5-3 megaOhms when filled with internal solutions. Whole-cell capacitance and series resistance were compensated with linear leak currents were digitally subtracted by P/4 method for voltage clamp experiments and bridge balance compensated in current clamp experiments. Signals were filtered at 10 kHz and digitized at 10-20 kHz. Cells wherein series resistance or bridge balance was over 15 megaOhm or fluctuated by more than 30% over the course of an experiment were omitted from datasets. Analysis was performed using Fitmaster software from HEKA and Origin9.0 software from OriginLab Corp.

Voltage Clamp Protocols.

DRGs were subjected to current-density (I-V) protocol (FIG. 11A) and H-infinity (prepulse inactivation protocol) (FIG. 11C). In the I-V protocol, cells were held at a −80 mV holding potential prior to depolarization by 20 ms voltage steps from −70 mV to +60 mV in 5 mV increments. This allowed for collection of current density data to analyze activation of sodium channels as a function of current versus voltage and also peak current density which was typically observed near ~0-10 mV and normalized to cell capacitance (pF). To estimate tetrodotoxin-resistant (TTX-R) contributions, the I-V protocol was run after incubation with 500 nM TTX. Following holding at −100 mV, 200 ms voltage steps from −70 mV to +60 mV in 5 mV increments allowed for analysis of peak currents. The TTX-R peak current density was always measured at depolarizations near 0 mV and within 10 ms of the voltage step protocol. Given the previously identified properties of NaV1.8 and NaV1.9 TTX-R currents, this voltage-dependence and activation profile indicates that the analysis of peak current density represents only NaV1.8 current (see, e,g., Maruyama H, et al., Pflugers Arch 2004; 449(1):76-87). Thus, sodium current present at 150 ms following a voltage pulse to −60 mV, was investigated, an established method of isolating Nav1.9 current.

In the H-infinity protocol, cells were held at −100 mV and subjected to conditioning voltage steps for 1 s varying from −120 mV to 0 mV in 10 mV increments. This conditioning step was followed by a 0 mV test pulse for 200 ms to analyze current. The H-infinity protocol allowed subtraction of electrically isolated TTX-R (current available after −40 mV prepulse) from total current (current available after −120 mV prepulse) to estimate tetrodotoxin-sensitive (TTX-S) current. This protocol is possible due to differential inactivation kinetics of TTX-R versus TTX-S channels wherein TTX-S current becomes activated and then fast-inactivated during the 1 s pulse to −40 mV. A visual representation of this protocol is presented in FIG. 10C. For all protocols, a test pulse was performed before and after the voltage protocol to evaluate run-down or run-up of currents during the voltage protocols and to exclude data from cells with currents that were altered as a function of time.

Samples Preparation for Proteomics.

DRG and dorsal horn of the spinal cord from rats exposed to ambient light or green LED (4 lux, 5 days, 8 hours/day) were isolated and lysates were prepared as described above. Proteins were precipitated using 100% ice-cold acetone and centrifuged at 15000×g at 4° C. for 10 min. The pellets, containing solubilized proteins, were re-suspended in 100 mM Tris pH=7.4, 8M urea (to eliminate carrying forward any salt contamination) and their protein content analyzed by mass spectrometry at the Arizona Proteomics Consortium after trypsin digestion.

Database Searching.

Tandem mass spectra were extracted. Charge state deconvolution and deisotoping were not performed. All MS/MS samples were analyzed using Sequest (Thermo Fisher Scientific, San Jose, Calif., version 1.3.0.339). Sequest was set up to search RattusNorvegicus_UniprotKB_2016_0406_cont.fasta assuming the digestion enzyme trypsin. Sequest was searched with a fragment ion mass tolerance of 0.80 Da and a parent ion tolerance of 10.0 PPM. Oxidation of methionine and carbamidomethyl of cysteine were specified in Sequest as variable modifications.

Criteria for Protein Identification.

Scaffold (version 4.5.1, Proteome Software Inc., Portland, Oreg.) was used to validate MS/MS based peptide and protein identifications. Peptide identifications were accepted if they could be established at greater than 20.0% probability to achieve a false discovery rate (FDR) less than 0.1% by the Scaffold Local FDR algorithm. Protein identifications were accepted if they could be established at greater than 100.0% probability and contained at least 5 unique peptides. Protein probabilities were assigned by the Protein Prophet algorithm (see, e.g., Nesvizhskii A I, et al., Anal Chem 2003; 75(17): 4646-4658). Proteins that contained similar peptides and could not be differentiated based on MS/MS analysis alone were grouped to satisfy the principles of parsimony. Proteins sharing significant peptide evidence were grouped into clusters. Proteins were annotated with gene ontology (GO) terms from gene_association.goa_uniprot (downloaded Jul. 5, 2013) (see, Ashbumer M, et al., Nat Genet 2000; 25(1):25-29).

Data Analysis.

The statistical significance of differences between means was determined by parametric analysis of variance (ANOVA) followed by post hoc comparisons (Student-Newman-Keuls test) using GraphPad Software. Pharmacological profiling of sensory neurons data was analyzed using Sigma Plot 12.5 and compared by z-test. Differences were considered to be significant if p≤0.05. All data were plotted in GraphPad Prism 6.

Results.

Antinociceptive Effects of Green LED.

Figure 2:
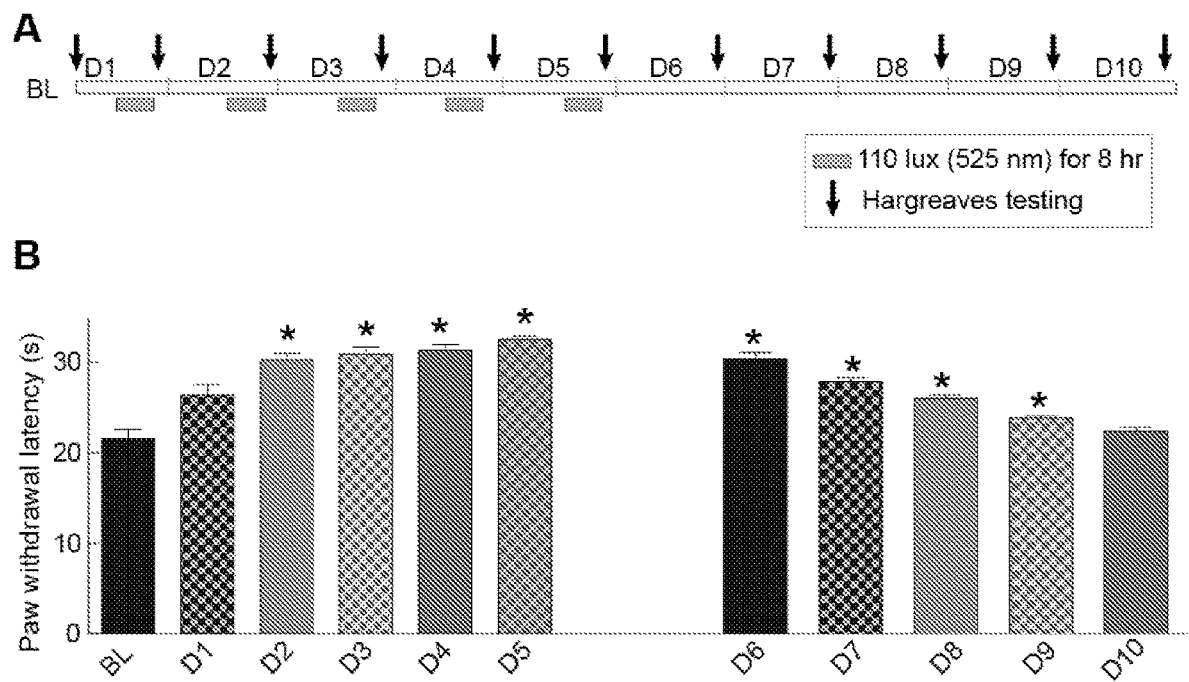
FIG. 2. Green light emitting diode (LED)-induced thermal analgesia—time course and duration of effect. (A) Schematic representation of the experimental design, LED exposures, and Hargreaves testing. (B) Bar graph showing the paw withdrawal latency (seconds) of rats (n=6 per group) treated as shown in the schematic in A. BL indicates the baseline latency before green LED exposure. Green LED exposure resulted in thermal analgesia starting at the second day (D2) of phototherapy and lasted 4 days after cessation (till D9) of LED exposure. *$p<0.05$ when comparing to BL (one-way ANOVA followed by Student-Newman-Keuls test).

It was determined if various kinds of light conditions affected pain-related behaviors in naïve rats. Rats were exposed, for eight hours, to ambient room light that consisted of white fluorescent lights and ambient sunlight through glass windows (600 lux), white LED (575 lux), or darkness (0 lux) and paw withdrawal latency (PWL) was measured. As shown in FIG. 1, the PWLs were unchanged across all conditions. In contrast, naïve rats exposed to green LED (525 nm wavelength; 110 lux) for eight hours daily for five days demonstrated a time-dependent increase in PWL that was significantly higher than rats exposed to ambient room light (FIG. 1). PWLs were also higher in rats exposed to blue LED (472 nm wavelength; 110 lux) but less than those exposed to green LED (FIG. 1). The increase in PWLs, elicited by green LED exposure, plateaued by the second day and was unchanged thereafter until the fifth day (FIG. 2B). The green LED exposure was terminated on day 5 and the PWLs were measured on subsequent days to determine if the increase in PWLs was transient or long-lasting (FIG. 2A). The increase in PWLs induced by green LED exposure was maintained for 4 days before returning to baseline (FIG. 2B).

Figure 3:
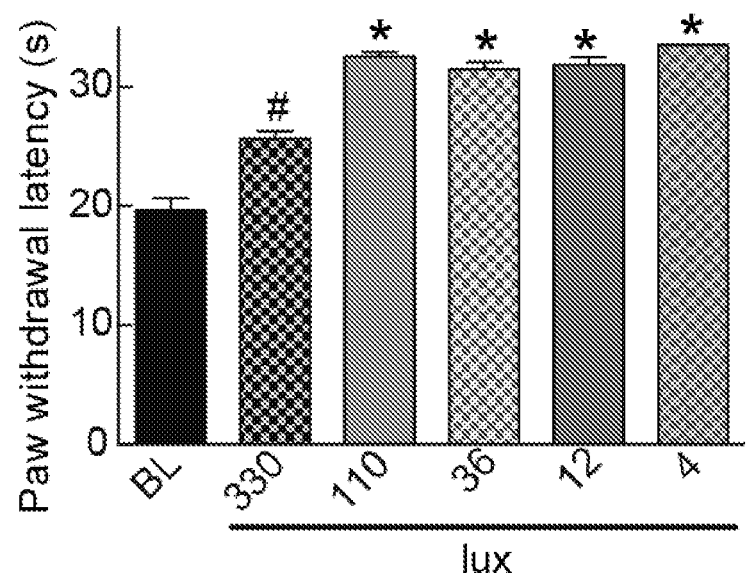
FIG. 3. Green light emitting diode (LED)-induced thermal analgesia—effect of level of illuminance. Bar graph of paw withdrawal latency (seconds) of rats (n=6 per group) exposed to the indicated illuminance level of green LED for eight hours daily for five days. BL indicates the baseline latency before green LED exposure. LED exposure Green LED exposure as low as 4 lux resulted in thermal analgesia. *$p<0.05$ when comparing to BL (one-way ANOVA followed by Student-Newman-Keuls test).

The preceding experiments were conducted with 110 lux green LED. However, whether this lux level was necessary and sufficient to elicit the antinociceptive behavior is not known. Consequently, the rats were exposed to green LED spanning several lux intensities. Exposing rats for eight hours to 4 lux green LED levels was sufficient for increasing PWLs compared with non-exposed rats (FIG. 3). Similar levels of PWLs were observed with rats exposed to 12, 36, or 110 lux green LED levels (FIG. 3). Exposure of rats to green LED 330 lux level significantly increased PWLs compared to baseline ambient-light exposed rats but was lower than all of the other lux conditions (FIG. 3). As the 4 lux green LED exposure for 8 hours was sufficient for achieving maximal antinociception, this lux level was used for all subsequent experiments.

Pharmacological Characterization of the Antinociceptive Effects of Green LED.

Figure 4:
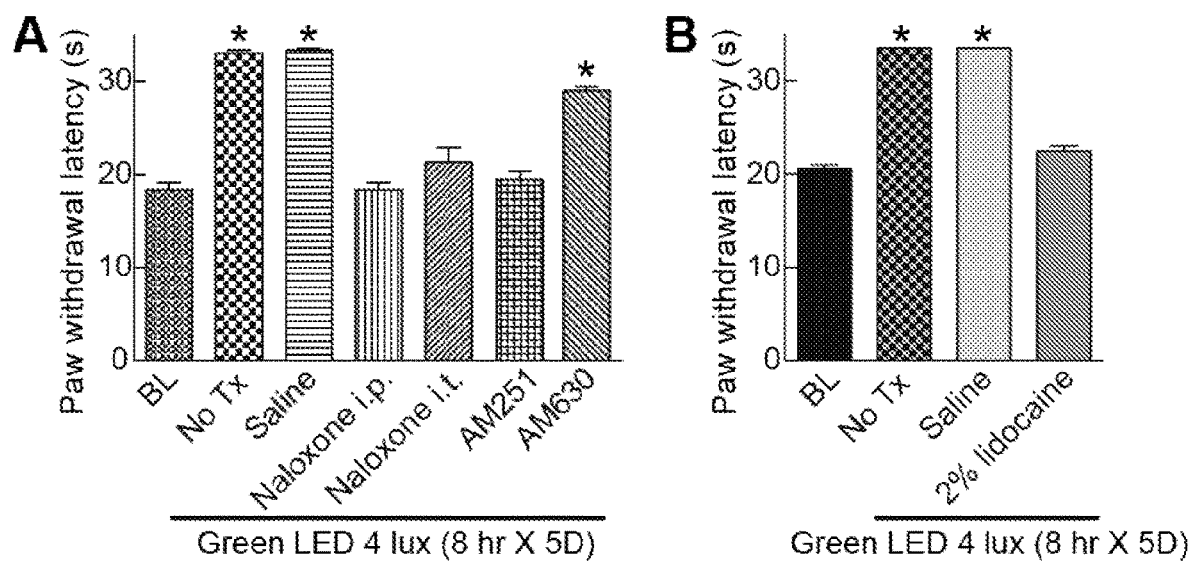
FIG. 4. Green light emitting diode (LED)-induced thermal analgesia involves activity of the descending pain pathways through endogenous opioid and cannabinoid signaling. (A) Bar graph of paw withdrawal latency (seconds) of rats (n=6 per group) prior to and after treatment with green LED as indicated. BL indicates the baseline latency before green LED exposure. Inhibiting mu-opioid receptor (MOR) with naloxone (intraperitoneal (i.p.) or intrathecal (i.t.) administration) or cannabinoid receptor 1 (CB1) with AM251 (see Table 1) reversed green LED-induced thermal analgesia which was unaffected by inhibition of cannabinoid receptor 2 (CB2) with AM630. Un-treated (No Tx) rats or rats injected i.p. with saline (n=6 per group) developed green LED-induced thermal analgesia. (B) Inactivation of the descending pathway pain with an injection of a 2% solution of lidocaine into the rostral ventromedial medulla (RVM) of rats (n=6 per group) reversed green LED-induced thermal analgesia. *$p<0.05$ when comparing to BL (one-way ANOVA followed by Student-Newman-Keuls test).

The antinociceptive effects of green LED indicates a possible involvement of endogenous mediators linked to pain, such as opioids and cannabinoids. To test this hypothesis, naïve rats exposed to green LED for eight hours daily for five days were administered antagonists and then PWLs were measured 20-30 minutes later. The green LED-induced antinociception was reversed, to baseline levels, following both subcutaneous or intrathecal administration of the mu opioid receptor (MOR) antagonist Naloxone (20 mg/kg i.p.). That a low dose (20 □g, i.t.) of intrathecal morphine also reversed the antinociception reveals that the site of action is likely central, as this dose of Naloxone; despite crossing the blood brain barrier, would not be expected to have peripheral effects (FIG. 4A). Systemic administration of the cannabinoid 1 (CB1) receptor antagonist/inverse agonist AM251 (1 mg/kg), but not the CB2 receptor antagonist AM630 (1 mg/kg), reversed the green LED-induced antinociception (FIG. 4A). These results demonstrate that green LED exposure likely elicits antinociception via release of endogenous opioids and cannabinoids.

Neurons within the rostral ventromedial medulla (RVM) have been reported to project to the spinal or medullary dorsal horns to directly or indirectly enhance or diminish nociceptive traffic (see, e.g., Zhang Y, et al., The Journal of clinical investigation 2015; 125(10):3782-3794). As this descending modulatory circuit is "opioid-sensitive", next the contribution of the RVM in the green LED-induced antinociceptive response was examined. Microinjection of 2% lidocaine into the RVM of naïve rats prevented the subsequent development of antinociception when the rats were exposed to green LED (FIG. 4B).

Figure 5:
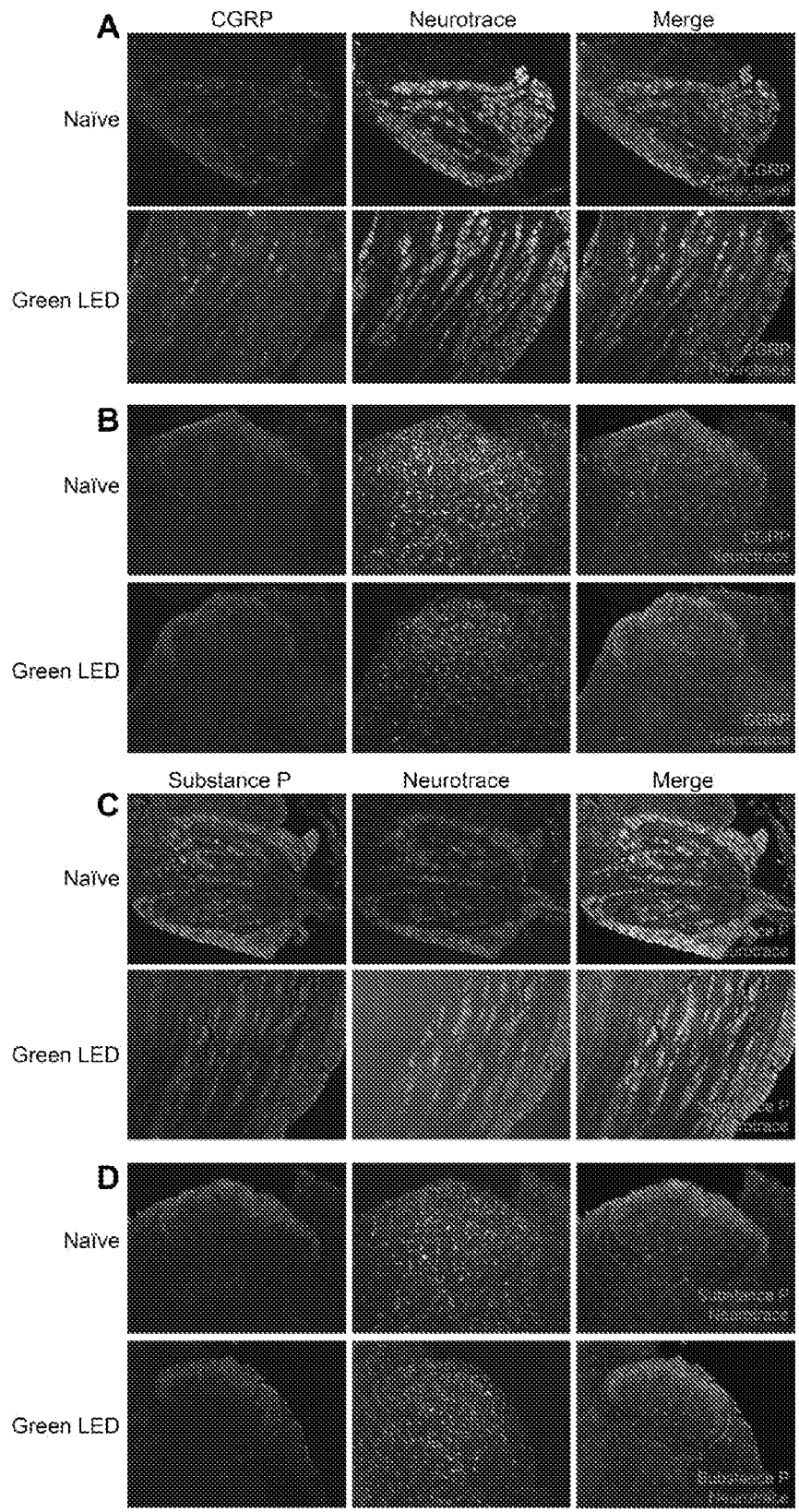
FIG. 5. Effect of green light emitting diode (LED) exposure on calcitonin gene related peptide (CGRP) and substance P (SP) in dorsal root ganglia (DRG) neurons and spinal cord. (A) Micrographs of a 10-μm sections of DRGs from either naïve (top panel) or green LED-exposed rats (bottom panel) double-immunostained with CGRP and Neurotrace, a marker of neuronal somas. Merge shows that the CGRP expression pattern in DRG neurons was similar between naïve and green LED exposed rats. (B) Representative micrograph of double-immunofluorescent staining for CGRP and Neurotrace in the dorsal horn of the spinal cord (lumbar region) from either naïve (top panel) or green light exposed rats (bottom panel). Merge shows CGRP expression pattern in dorsal horn was similar between naïve and green LED exposed rats. (C) Double-immunofluorescent staining for Substance P and Neurotrace in DRGs from either naïve (top panels) or green light exposed rats (bottom panels). Merge shows Substance P expression pattern in DRG neurons was similar between naïve and green LED exposed rats. (D) Representative micrograph of double-immunofluorescent staining for Substance P and Neurotrace in the dorsal horn of the spinal cord (lumbar region) from either naïve (top panels) or green light exposed rats (bottom panels). Merge shows Substance P expression pattern in dorsal horn was similar between naïve and green LED exposed rats.

While the data thus far shows a central role for the endogenous opioid and cannabinoid system, it is possible that the exposure conditions may physically stress the rats. Reportedly, physical stress induces antinociception in animals and the evidence demonstrates involvement of the alpha and beta-adrenergic system and the opioid system in this process (see, e.g., Takahashi M, et al., Jpn J Pharmacol 1984; 35(2):175-179; Spradley J M, et al., Pain 2012; 153(9):1890-1897; Maier S F. Ann N Y Acad Sci 1986; 467:55-72; Lewis J W, et al., Science 1980; 208(4444):623-625; Butler R K, Finn D P. Prog Neurobiol 2009; 88(3): 184-202; Bodnar R J, et al., Pharmacol Biochem Behav 1980; 13(2):171-175). Thus, to elucidate the role of the adrenergic system, several adrenergic receptors antagonists were tested. Phenoxybenzamine, a nonselective irreversible alpha-blocker; Phentolamine, a nonselective alpha-blocker; and propranolol, a nonselective beta-blocker all failed to prevent or reverse the antinociceptive effect of green LED (FIG. 5). Additionally, rats exposed to green LED maintained regular grooming behaviors, which is in contrast to diminished grooming observed in stressed rats (see, e.g. Katz R J, et al., Neuroscience letters 1979; 13(2):209-212). Collectively, these results show that green LED induced antinociception is not invoking a stress response in these rats.

Green LED-Induced Analgesia Does Not Involve Alterations in CGRP and Substance P Expression.

Figure 6:
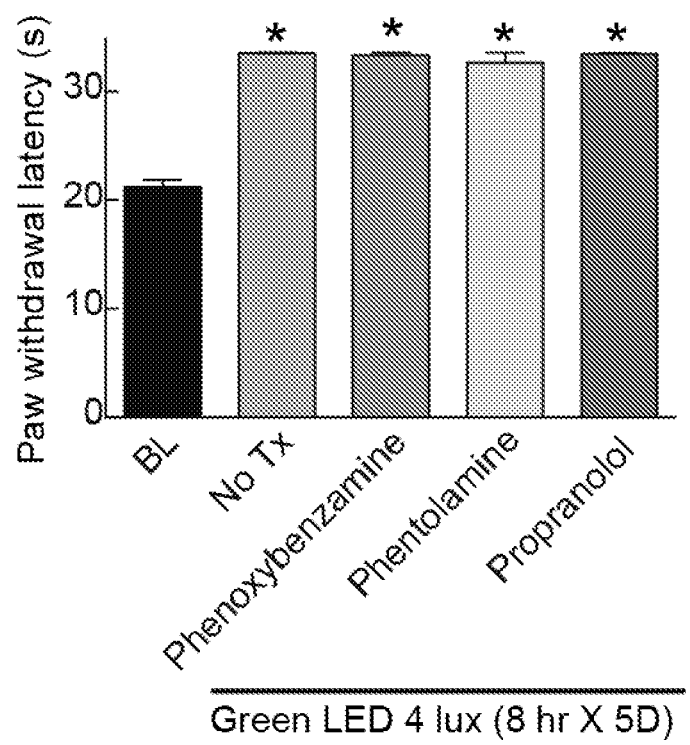
FIG. 6. Green light emitting diode (LED)-induced thermal analgesia does not invoke a stress response. Bar graph of paw withdrawal latency (seconds) of rats (n=6 per group) prior to and after treatment with green LED as indicated. BL indicates the baseline latency before green LED exposure. Inhibiting the alpha- (with Phenoxybenzamine or Phentolamine) or beta- (with propranolol) adrenergic receptors (see Table 1) failed to reverse green LED-induced thermal analgesia. *$p<0.05$ when comparing to BL (one-way ANOVA followed by Student-Newman-Keuls test).

Next, expression patterns in DRG and dorsal horn slices of neurotransmitters calcitonin gene related peptide (CGRP) and substance P, both of which are key in the nociceptive signal transduction pathway were assessed. Staining for CGRP was observed in neuronal somas (stained with neurotrace) in DRGs from both naïve and green LED exposed rats (FIG. 6A). In the dorsal horn of the spinal cord, CGRP staining showed a robust expression in the pre-synaptic terminals located in laminae I and II in both naïve and Green LED exposed rats (FIG. 6B). However, no significant differences in CGRP expression pattern were observed in tissues from naïve or Green LED exposed rats. All neuronal somas showed Substance P expression in DRGs from both naïve and Green LED exposed rats (FIG. 6C). In the dorsal of the spinal cord, Substance P was expressed by the pre-synaptic terminals located in laminae I and II in both naïve and Green LED exposed rats (FIG. 6D). No significant differences in Substance P expression pattern were observed in tissues from naïve or Green LED exposed rats. These results rule out alterations of nociceptive neurotransmitter expression in either DRG or dorsal horn as a possible mechanism underlying green LED-induced analgesia.

Characterization of the Role of the Visual System in the Antinociceptive Effects of Green LED.

Figure 7:
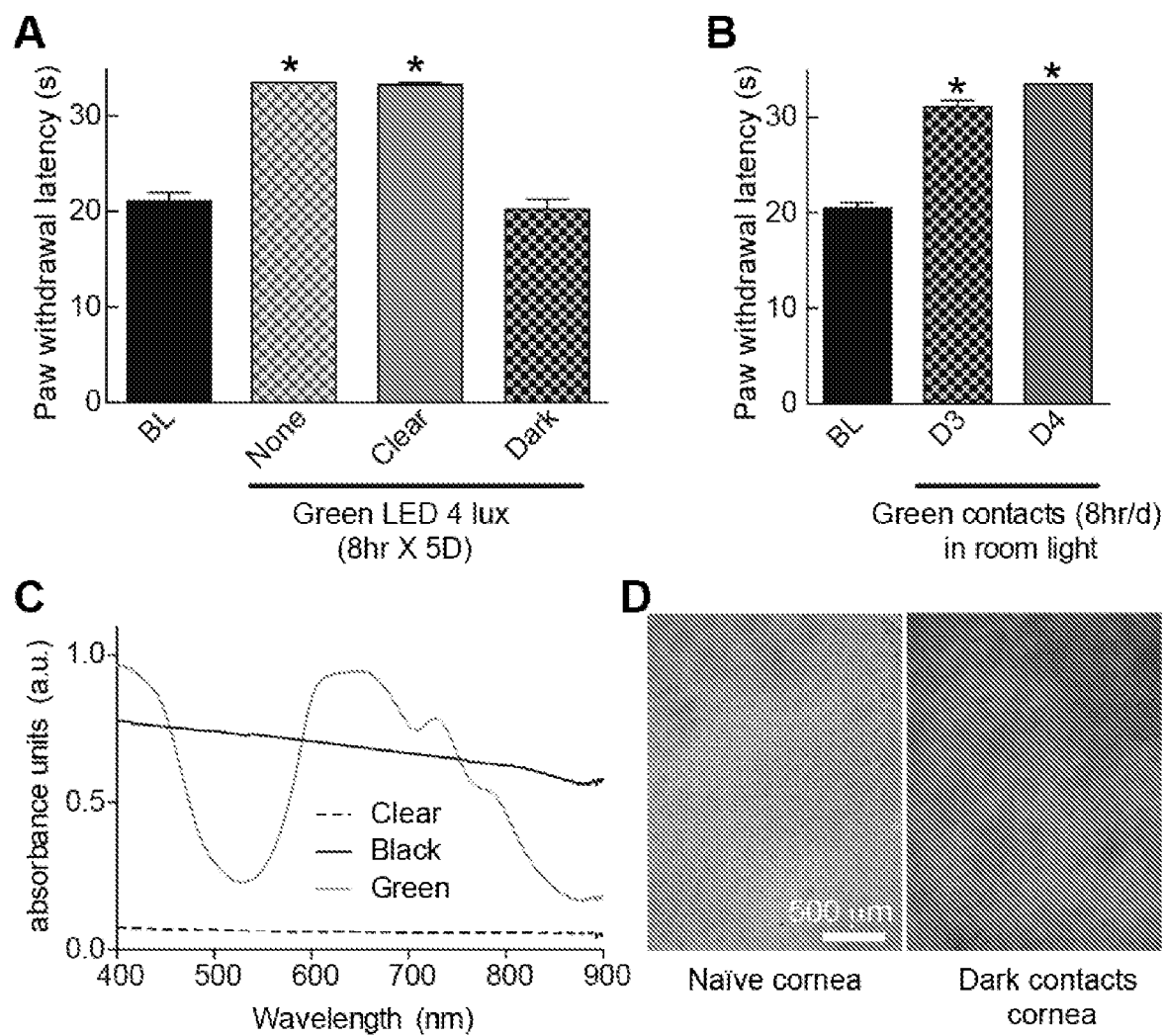
FIG. 7. Involvement of the visual system in green light emitting diode (LED)-induced thermal analgesia. (A) Bar graph of paw withdrawal latency (seconds) of rats (n=6 per group) prior to and after treatment with green LED as indicated. During the green LED exposure paradigm, the rats were fitted with clear or dark plastic lenses on their eyes. Blocking green LED absorbance to the eyes with dark contacts prevented the development of green LED-induced thermal analgesia. (B) Rats 'wearing' green plastic eye contacts and exposed to ambient room light for eight hours daily developed thermal analgesia on days 3 and 4. *$p<0.05$ when comparing to baseline (BL) (one-way ANOVA followed by Student-Newman-Keuls test). (C) Absorbance spectra, in arbitrary units (a.u.), of clear, dark, or green contacts. Dark contacts absorbed light in all wavelengths while green contacts showed a peak absorbance in the 580-700 nm range. (D) Representative micrographs of Evans blue dye-stained rat corneas. No pathological damage was noted in corneas from rats 'wearing' dark contacts compared to corneas from rats 'wearing' no contacts.

Since light is an external stimulus, the possibilities of its route of action may be either via the visual system through the retina or the skin. To distinguish between these possibilities, dark opaque plastic contact lenses that permitted no light penetration were produced and fitted onto the rats' eyes under anesthesia. As a control, transparent clear lenses were also installed onto other rats's eyes. Both groups of rats were then exposed to green LED for eight hours daily for five days and their PWLs were monitored. Following this exposure paradigm, rats fitted with the dark, opaque contact lenses failed to develop antinociception, whereas rats fitted with clear, transparent contact lenses developed antinociception similar to rats with no contacts (FIG. 7A). Consistent with the importance of the visual system in the development of green LED-induced antinociception, rats fitted for eight hours with "green" contacts that permit light transmission in the green part of the visual spectrum (FIG. 7B), developed antinociception when exposed to room light (FIG. 7C). Importantly, histological analysis of the eyes of the rats at the end of the experiments revealed no damage caused by either contact lens (FIG. 7D). These results support a role for the visual system in mediating the green LED mediated antinociception.

Figure 8:
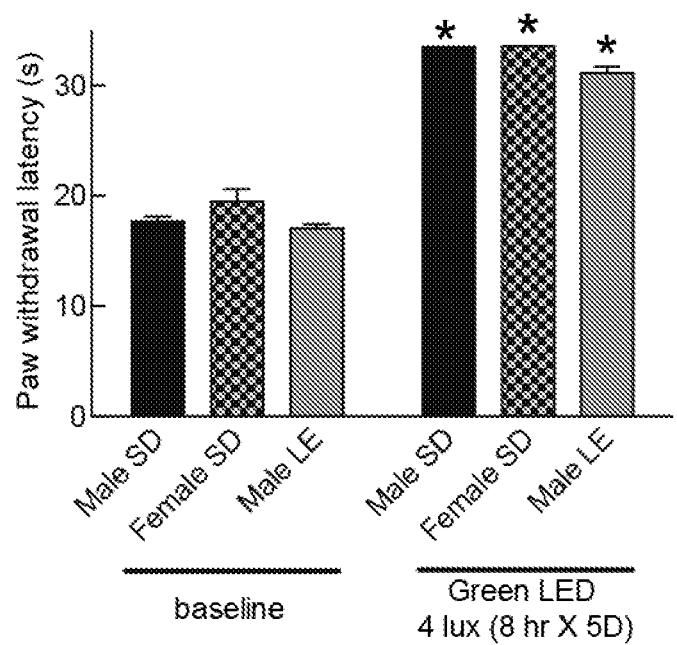
FIG. 8. Green light emitting diode (LED)-induced thermal analgesia does not rely on skin pigmentation and occurs in both genders. Bar graph of paw withdrawal latency (seconds) of male and female Sprague-dawley rats (SD, white fur) and male long-evans (LE) rats (n=6 per group) prior to and after treatment with green LED as indicated. All rats developed thermal analgesia compared to their own baseline. *p<0.05 when comparing to baseline (one-way ANOVA followed by Student-Newman-Keuls test).

To test if pigmented skin is involved in the antinociceptive effects of green LED, pigmented Long Evans (LE) rat, which are different from the albino Sprague-Dawley (SD) rats that lack pigmentation, were used. A similar level of antinociception was observed in SD or LE rats exposed to green LED for eight hours daily for five days; the PWLs were significantly higher than the respective strains exposed to ambient light (FIG. 8). The antinociceptive was not restricted to male rats as female SD rats exposed to the same green LED paradigm also exhibited increased PWLs (FIG. 8). Collectively, these results indicate that pigmentation is not important for developing antinociception.

Exposure to Green LED Does Not Impair Motoric Performance.

Figure 9:
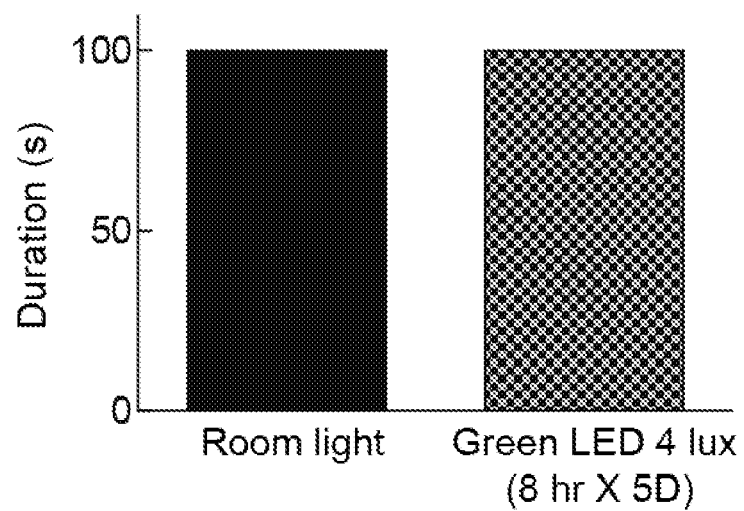
FIG. 9. Motor function is not affected by green light emitting diode (LED) treatment. Bar graph of latency of rats (n=6 per group) to fall off the rotarod at incremental speed. Thermal analgesia induced by green LED exposure did not impair motoric performance as there were no differences between the fall off latencies between these and rats exposed to ambient room light. p>0.05 when comparing between the two conditions (Student's t test).

If, following exposure to green LED, the rats had a reduced motor activity, then this could contribute to the antinociception. To test this possibility, it was investigated if the green LED exposure affected motor performance using the rotarod assay. Following verification of antinociceptive behaviors induced by exposure to green LED for eight hours daily for five days exhibited antinociception, no change in the ability of the rats to stay on the rotation rod (FIG. 9) was observed. Thus, repeated green LED exposure does not affect motor performance.

Functional 'Fingerprinting' of Sensory Neurons from Green LED Exposed Rats.

To investigate neuronal changes that may have occurred in sensory neurons following green LED exposure, pharmacological profiling of neuronal populations was performed. DRG cultures were prepared from rats after exposure to green LED for eight hours daily for five days or control conditions and their functional profiling performed with by $Ca^{2+}$ imaging as described recently (see, e.g., Moutal A, Chew L A, Yang X, Wang Y, Yeon S K, Telemi E, Meroueh S, Park K D, Shrinivasan R, Gilbraith K B, Qu C, Xie J Y, Patwardhan A, Vanderah T W, Khanna M, Porreca F, Khanna R. (S)-Lacosamide inhibition of CRMP2 phosphorylation reduces postoperative and neuropathic pain behaviors through distinct classes of sensory neurons identified by constellation pharmacology. Pain 2016). This approach allows us to characterize the molecular changes occurring in the sensory neurons after light exposure and may reveal light-induced changes leading to antinociception.

Figure 10:
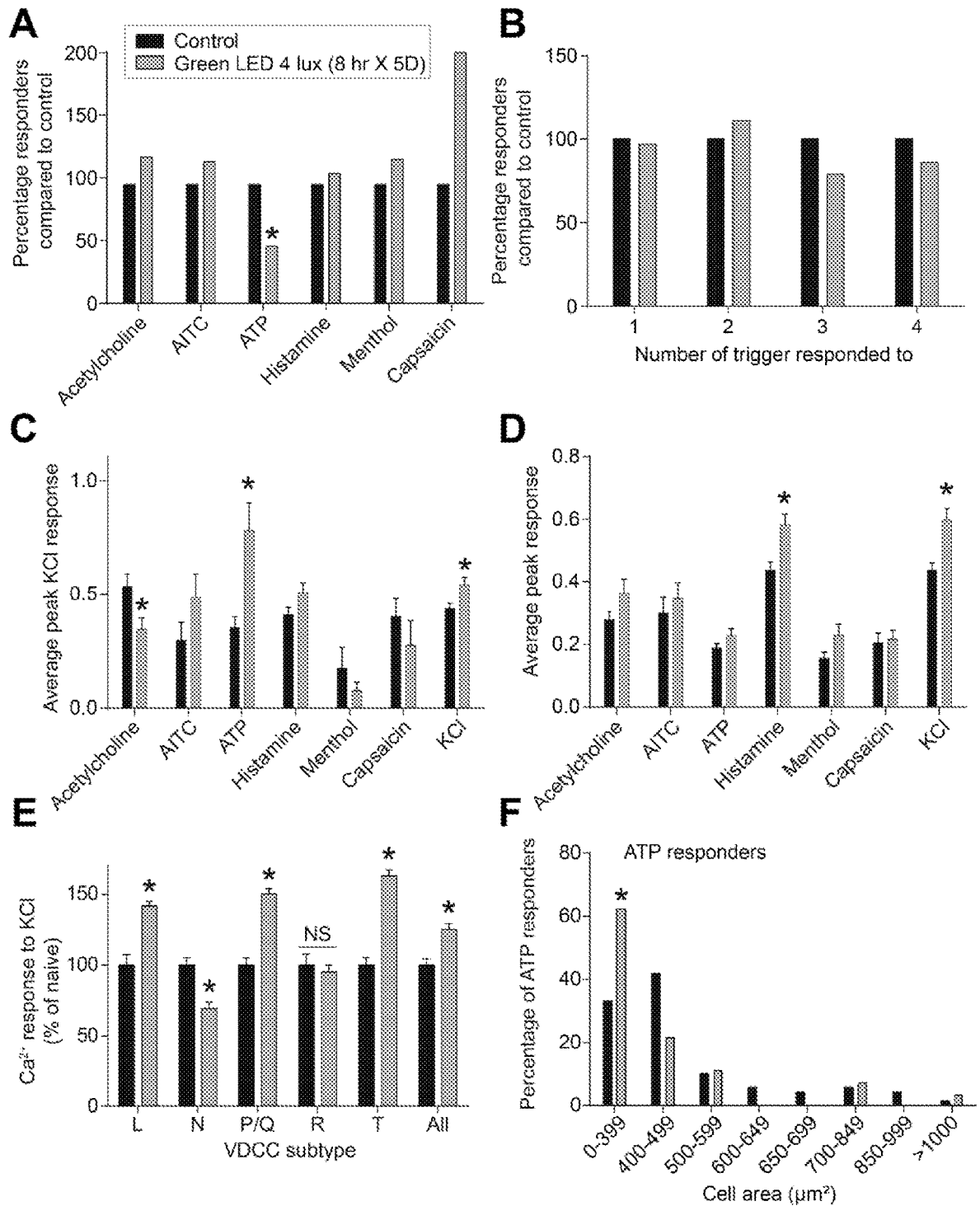
FIG. 10. Pharmacological profiling of dorsal root ganglia (DRG) neuronal subclasses following green light emitting diode (LED) exposure. (A) Bar graph of percent of cells, normalized to control (i.e., ambient light exposure), responding to each constellation trigger independently of any other trigger that the cell also responded to. The receptor agonists/triggers used were: acetylcholine (1 mM), allyl isothiocyanate (AITC; 200 µM), ATP (10 µM), histamine (50 µM), menthol (400 nM), or capsaicin (100 nM). All cells were selected based on their response to a depolarizing pulse of KCl (90 mM). Sensory neurons from green LED exposed rats had a decreased proportion of cells responding to ATP (z-test). (B) The response of DRG neurons to one or more receptor agonist was analyzed. The bar graph indicates the percentage of cells, normalized to control conditions, which responded to the indicated number of triggers. The number 1 corresponds to the proportion of cells that responded to KCl only and no other trigger. No significant change was observed in each category of cells between control condition and green LED exposure. (C) Bar graph of average peak KCl response in different functional neuronal populations defined by their response to indicated receptor agonist. Sensory neurons from green LED exposed rats, showed a decreased response to KCl among the acetylcholine-sensitive neurons and an increased response to KCl in the ATP-sensitive neurons (*p<0.05; one-way ANOVA). (D) Bar graph of average peak calcium response elicited by each receptor agonist in DRG neurons prepared from green LED exposed or control rats. Significant increases in average peak response for histamine and KCl were observed (*p<0.05; one-way ANOVA). (E) Bar graphs of sizes of neurons responding to ATP. Data are from 2 independent experiments with a total n=186 cells from control rats and n=161 from green LED exposed rats. (F) Bar graph of the normalized peak fluorescence response of DRGs prepared from green LED exposed or control rats in the presence of pharmacological blockers (see Methods for details) specific for the indicated calcium channel subtypes. Values represent the average±S.E.M., n=71-206 cells per condition. Asterisks indicate statistical significance compared with DRGs from ambient light exposed rats (i.e., control)(p<0.05, Student's t-test).

The proportion of sensory neurons responding to each receptor agonist challenge was assessed and a significant decrease of the proportion of sensory neurons responding to ATP in green LED exposed rats compared to control was observed (FIG. 10A). Although, there is a trend towards an increased percentage of neurons responding to capsaicin, from green LED exposed rats, the change did not reach statistical significance (p=0.065 compared with control) (FIG. 10A). These results demonstrate functional changes induced by green LED exposure in sensory neurons.

It was then asked if green LED exposure could alter the overall competence of the sensory neurons to respond to one or more receptor agonist challenges. No change of functional competence in sensory neurons isolated from green LED exposed rats compared to rats exposed to ambient light was observed (FIG. 10B), showing that the antinociception provided by green light exposure does not arise from a desensitization of the sensory neurons.

Next, to analyze how different types of sensory neurons could be altered by light exposure, the capacity of sensory neurons to respond to depolarization-induced $Ca^{2+}$ influx was investigated as voltage gated $Ca^{2+}$ channel activity has been directly linked to neurotransmitter release (see, e.g., Maggi C A, et al., Neuroscience letters 1990; 114(2):203-206; Kress M, et al., Neuroreport 2001; 12(4):867-870). Here, it was found that green LED exposure decreased depolarization-induced $Ca^{2+}$ influx in acetylcholine (Ach)-sensitive neurons (FIG. 10C). In contrast, ATP responding neurons, from rats exposed to green LED, had an increased depolarization-induced $Ca^{2+}$ influx (FIG. 10C). Next, it was investigated if the $Ca^{2+}$ influx elicited by each receptor agonist varied after green LED exposure. An increased $Ca^{2+}$ influx triggered by histamine application in neurons prepared from green LED exposed rats was observed (FIG. 10D). A global increase of the depolarization-induced $Ca^{2+}$ influx in sensory neurons prepared from green LED exposed rats was also observed (FIG. 10D), showing a greater activity of the voltage-gated $Ca^{2+}$ channels.

After having determined that sensory neurons isolated from green LED exposed rats had a decreased capacity to respond to ATP and have a trend toward increased capacity to respond to capsaicin, it was investigated if these changes were due to a specific neuronal population. To do so, the sensory neuron populations were stratified based on their cell surface areas. No specific cell population enriched between the capsaicin responding sensory neurons from green LED exposed rats compared to control rats was identified. A decreased proportion of neurons responding to ATP in the green LED exposed rats was observed, there were significantly more small sized neurons responding to ATP (FIG. 10E). All the other neuronal size subclasses were decreased, but did not reach statistical significance (FIG. 10E). These results indicate a dramatic change in the neuronal population responding to ATP. Taken together, these results indicate that green LED exposure results in a gain of ATP responding competence on the small size sensory neurons, which are likely involved in nociception. These neurons have an increased response to depolarization-induced $Ca^{2+}$ influx that could result in a greater ability to signal through antinociceptive pathways involving ATP, and possibly, L-type voltage-gated $Ca^{2+}$ channels. Thus, each $Ca^{2+}$ channel subtype was pharmacologically isolated to assess the effects of green LED exposure on each subtype. $Ca^{2+}$ influx via L-, P/Q-, and T-type channels was increased in DRG neurons from green LED exposed rats compared to control DRG neurons (FIG. 10F). In contrast, there was no difference in $Ca^{2+}$ influx via R-type channels between the DRG neuron populations while $Ca^{2+}$ influx via the N-type channel was decreased in green LED exposed rat DRG neurons (FIG. 10F).

Characterizing Sodium Currents in Sensory Neurons from Green LED Exposed Rats.

Figure 11:
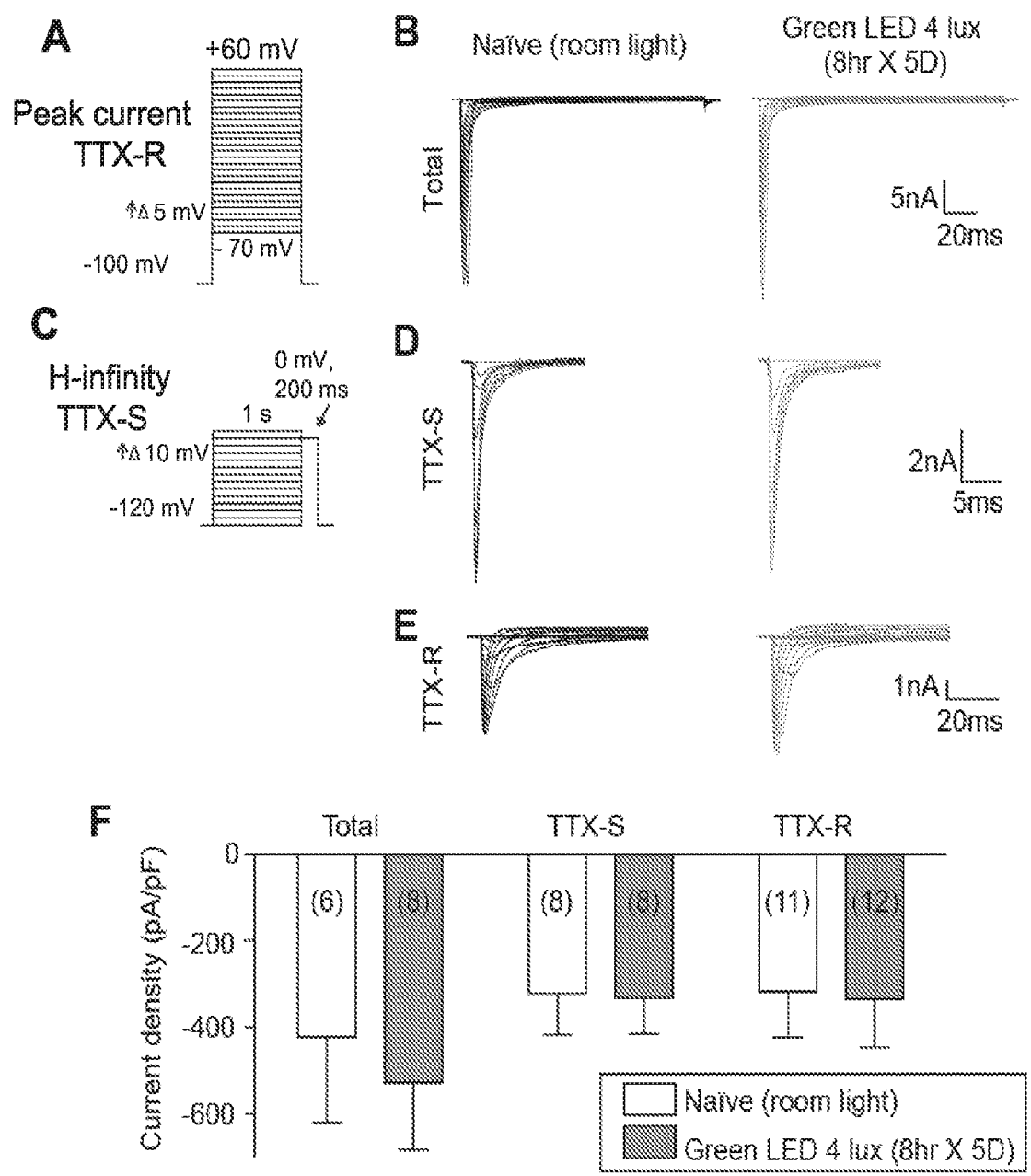
FIG. 11. Voltage-gated sodium currents in rat dorsal root ganglia (DRG) neurons are not affected by green light emitting diode (LED) exposure. (A) Voltage protocol used to evoke tetrodotoxin-resistant (TTX-R) $Na^+$ currents. (B) Representative family of total $Na^+$ currents in DRG neurons from naïve and green LED exposed rats. (C) Voltage protocol used to evoke tetrodotoxin-sensitive (TTX-S) $Na^+$ currents. Representative family of TTX-S (D) and TTX-R (E) $Na^+$ currents in DRG neurons from naïve and green LED exposed rats. (F) Summary of the peak current density (pA/pF) from DRG neurons (n=6-12 as indicated in parentheses within the bars) cultured from either naïve or green LED exposed rats. No significant difference was observed for total, TTX-S or TTX-R $Na^+$ current between naïve and green light LED treatment (p>0.05, Student's t test).

The properties of sodium currents have been proposed to be important for neuronal sensitization (see, e.g., Blair N T, et al., The Journal of neuroscience: the official journal of the Society for Neuroscience 2002; 22(23):10277-10290). Therefore the possible contribution of TTX-R $I_{Na}$ and TTX-S $I_{Na}$ to sensitization was examined. In small diameter sensory neurons, tetrodotoxin (TTX) can be used to separate total $I_{Na}$ into those currents that are sensitive (TTX-S, predominantly NaV1.1 and NaV1.6) and resistant (TTX-R, predominantly NaV1.8) to blockage by this toxin (see, e.g., Roy M L, et al., The Journal of neuroscience: the official journal of the Society for Neuroscience 1992; 12(6):2104-2111). Representative traces for total, TTX-S, and TTX-R $I_{Na}$ in DRG neurons from ambient (room) light and green LED exposed rats are shown in FIG. 11. None of these currents were changed between the two DRG populations (FIG. 11F). Additionally, the voltage dependence for activation of the currents was also nearly the same between the two DRG populations (data not shown). These results indicate that the sodium currents do not contribute to the green LED-induced analgesia.

Proteomics Reveals Potential Mechanism for Green LED-Induced Analgesia.

Figure 12:
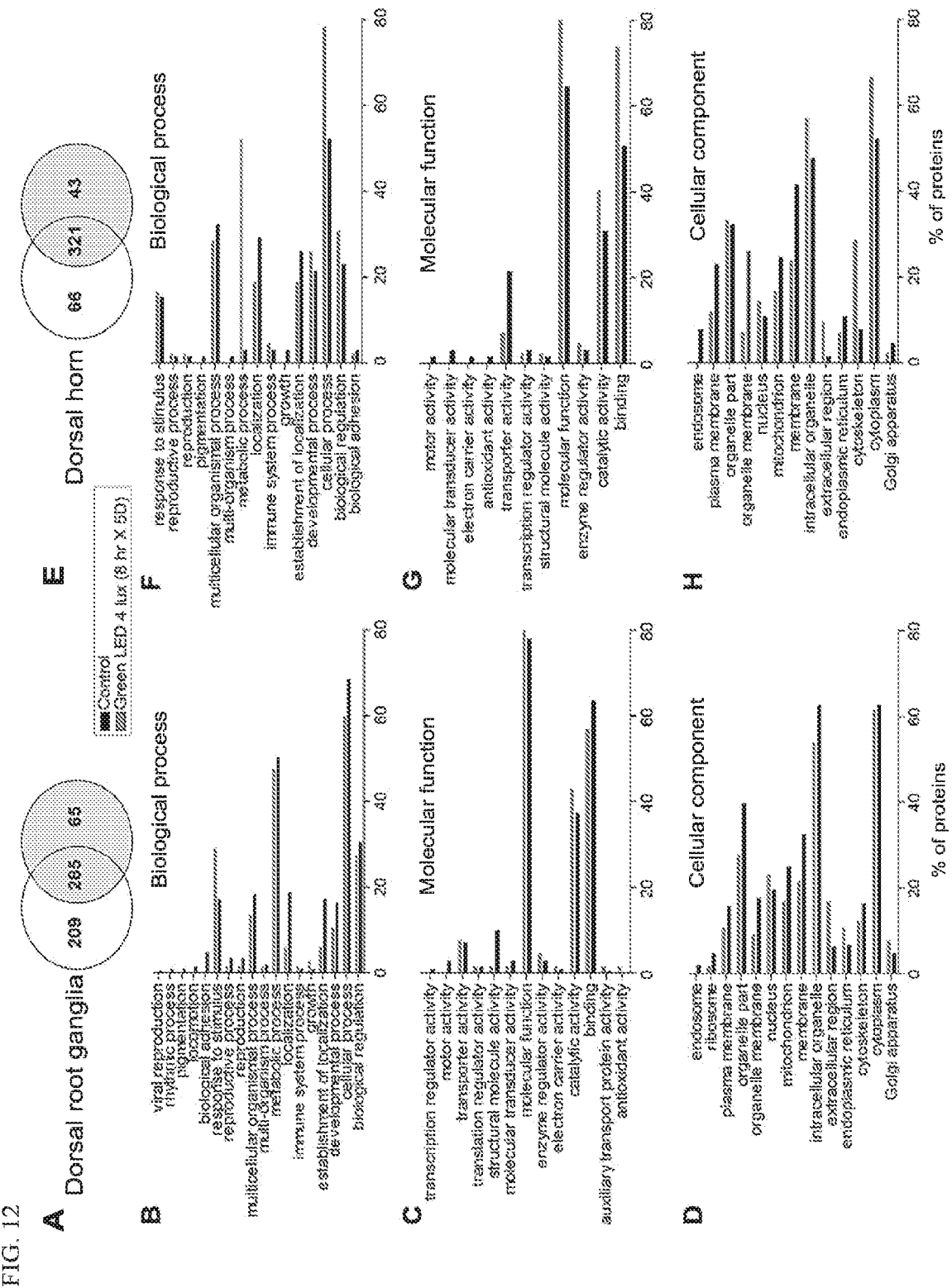
FIG. 12. Comparative proteomic analysis of dorsal root ganglia (DRG) and dorsal horn (DH) of the spinal cord from rats exposed ambient or green light emitting diode (LED) using one-dimensional-liquid chromatography-electrospray ionization-tandem mass spectrometry. Venn diagram of the identified proteins in control and green LED exposed rat DRG (A) and dorsal horn of the spinal cord (E). Biological process (B, F), molecular function (C, G), and cellular component (D, H) were analyzed using the Proteome software Scaffold. The numbers indicate the percent of proteins detected in the proteomic study that are clustered in the annotated groups from naïve (black) or green LED exposed rats (green).

An unbiased-proteomics approach was used to identify possible protein alterations, using liquid chromatography-tandem mass spectrometry (LC-MS/MS), in tissues from ambient versus green LED exposed rats. Among 559 non-redundant protein identified in the DRG samples (Lumbar levels 4, 5 and 6 were pooled), 65 proteins were detected only in DRGs from green LED treated rats (FIG. 12A). Gene ontology (GO) terms corresponding to the biological processes (FIG. 12B), molecular functions (FIG. 12C), and cellular component (FIG. 12D) of these proteins identified in DRGs were extracted and compared between ambient and green LED exposed rats. A higher number of proteins associated with the "response to stimulus" category and a fewer proteins associated with "growth" category in DRGs from green LED exposed rats compared to DRGs from ambient room light exposed rats were observed (FIG. 12B). The molecular functions associated with these proteins indicates a decreased "structural molecule activity" and an increased "antioxidant activity" in DRGs from rats with green LED-induced thermal analgesia compared to controls (FIG. 12C). Finally, fewer proteins from green LED DRGs appear to be localized in "organelle part" and "membrane" (FIG. 12D).

Figure 13:
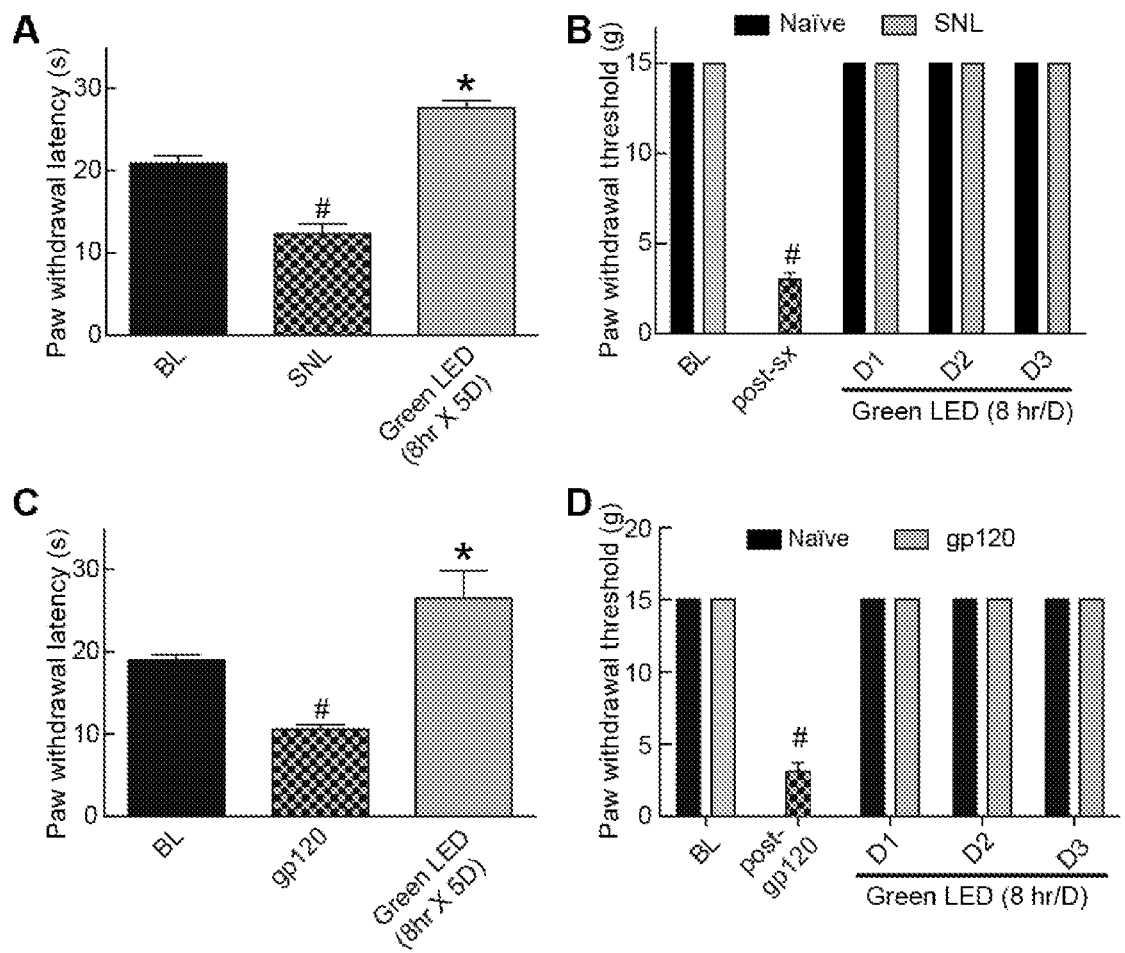
FIG. 13. Exposure to green light emitting diode (LED) reverses thermal hyperalgesia and mechanical allodynia induced in two models of neuropathic pain. (A) Seven days following a spinal nerve ligation (SNL) surgery on their left hind paw, rats (n=6 per group for all groups throughout this figure) displayed a significant decrease in their paw withdrawal latencies (seconds), which was completely reversed by daily eight hours exposure to green LED exposure (4 lux). #p<0.05 when comparing to BL, *p<0.05 when comparing to BL or SNL (one-way ANOVA followed by Student-Newman-Keuls test). (B) Bar graph of paw withdrawal thresholds (PWTs, grams) of rats after receiving a SNL injury and after green LED exposure during either 1, 2 or 3 days (4 lux, 8 hours per day). BL indicates the baseline PWT before green LED exposure. PWTs were significantly reversed after 1, 2 or 3 days of green LED exposure compared to post-surgery (post-Sx) levels. #p<0.05 compared to BL (one-way ANOVA followed by Student-Newman-Keuls test). (C) Seven to ten days following an intrathecal injection of the HIV-1 envelope glycoprotein gp120, rats displayed a significant decrease in their paw withdrawal latencies (seconds), which was completely reversed by daily eight hours exposure to green LED exposure (4 lux). #p<0.05 when comparing to BL, *p<0.05 when comparing to BL or gp120 (one-way ANOVA followed by Student-Newman-Keuls test). (D) (B) Bar graph of PWTs of rats after receiving a gp120 injection and after green LED exposure during either 1, 2 or 3 days (4 lux, 8 hours per day). BL indicates the baseline PWT before green LED exposure. PWTs were significantly reversed after 1, 2 or 3 days of green LED exposure compared to post-gp120 levels. #p<0.05 compared to BL (one-way ANOVA followed by Student-Newman-Keuls test).

A total of 430 non-redundant proteins were identified in dorsal horn tissues, of which 43 were found only in the samples from rats with green LED-induced thermal analgesia (FIG. 12E). A higher number of proteins associated with "metabolic process" and "cellular process" categories in dorsal horn from green LED exposed rats was observed compared to dorsal horn from ambient room light exposed rats (FIG. 12F). The molecular functions associated with these proteins indicates a decreased "transporter activity" and an increased "binding" functions in dorsal horn from rats with green LED-induced thermal analgesia compared to controls (FIG. 13G). Finally, more proteins were observed to be in "cytoskeleton" and "intracellular organelles" while fewer proteins noted in "membrane", "plasma membrane" and "organelle membrane" in dorsal horn from green LED exposed rats compared to dorsal horn from ambient room light exposed rats (FIG. 12H). Thus, fewer proteins are localized in membranes in dorsal horn, which is correlated, with fewer proteins implicated in localization processes in DRGs.

Analgesic Effects of Green LED Exposure in Two Models of Neuropathic Pain.

Having determined that green LED is antinociceptive in naïve animals, it was next asked if this non-pharmacological paradigm could be effective in reversing allodynia and hyperalgesia associated with two established experimental models of neuropathic pain. The first model—spinal nerve ligation (SNL) involves ligation of the L5 and L6 spinal nerves and results in persistent thermal hypersensitivity and tactile allodynia (see, e.g., Kim K J, et al., Experimental brain research Experimentelle Hirnforschung Experimentation cerebrale 1997; 113(2):200-206). Probing the plantar surface of the hindpaw ipsilateral to the side of nerve injury in SNL rats, 7 days post injury, revealed thermal hyperalgesia (FIG. 13A) and tactile allodynia (FIG. 13B). Exposing SNL-injured rats for eight hours daily to 4 lux green LED levels resulted in complete reversal of thermal hyperalgesia; the latencies were significantly higher than baseline so as to be antinociceptive (FIG. 13A). Paw withdrawal thresholds were also fully reversed by a single eight-hour exposure to green LED and remained elevated throughout the 3 days of green LED exposure (FIG. 13B).

The second model—distal symmetrical sensory peripheral neuropathy is frequently (30-60%) observed in people infected with Human Immunodeficiency Virus Type 1 (HIV-1) (see, e.g., Manji H. Current opinion in neurology 2000; 13(5):589-592). In rats injected with HIV-1 envelope glycoprotein gp120, robust thermal hyperalgesia (Hargreaves tests) and mechanical allodynia (von Frey tests) has been observed (see, e.g., Milligan E D, et al., The Journal of neuroscience: the official journal of the Society for Neuroscience 2001; 21(8):2808-2819; Yuan S B, et al., Annals of neurology 2014; 75(6):837-850). Intrathecal (i.t.) gp120 produced a thermal hyperalgesia that was fully reversed by exposing gp120-injected rats to eight hours daily of 4 lux green LED levels (FIG. 13C). I.t. gp120 lowered thresholds for paw withdrawals compared to baseline (i.e. pre-gp120); this mechanical allodynia was reversed by a single eight-hour exposure to green LED and remained elevated throughout the 3 days of green LED exposure (FIG. 13D). These results indicate that green LED exposure can reduce neuropathic pain behaviors.

Example 2

This example describes the effect of green LED exposure on pain reduction for certain human subjects having certain diagnosed disorders (see, Table 3). Male and female adults 18 years or older with chronic pain such as migraine or fibromyalgia were recruited from the chronic pain clinic at the University of Arizona-Banner clinic. Patients were randomized into either the green light treatment group or the control group (white light). Patients were provided with green LED light rope (GLED) or white LED rope. The intensity of the LED ropes was adjusted to be between 4-100 LUX (unit of measuring light intensity). Patients were asked to expose themselves to their assigned color for 1-2 hours every night for 10 weeks while eliminating any other light source to minimize light pollution. Patients were given four paper surveys to document the following:

Time log: Patients enter the time of light exposure every night

Analgesic log: Patients enter the amount of pain medication they use everyday while on the light therapy.

EQ-5D-5L: A survey to measure quality of life

A modified Pan clinic survey: A survey to measure the intensity of pain (on a scale from 0-10), the percentage of pain improvement in terms of intensity, frequency, and duration. It also measure the improvement of Ability to fall asleep, stay asleep, perform daily chores, daily activity, and exercise.

TABLE 3

| Age | Gender | Diagnosis | LED type | % pain reduction |
|---|---|---|---|---|
| 74 | F | Fibromyalgia | Green | 43% |
| 43 | F | Fibro/Migraine | Green | 28% |
| 51 | F | Fibro/Migraine | Green | 57% |
| 47 | M | Fibro/cervical radiculopathy | Green | 50% |
| 71 | F | Neuropathy | White | 0 |
| 58 | F | Fibromyalgia | White | 0 |
| 58 | F | Fibro/CRPS | White | Withdrew |
| 38 | F | Fibro/SLE | White | Withdrew |

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

The invention claimed is:

1. A method of treating pain, comprising:
    administering blue or green spectrum light to retina of a subject exhibiting pain under conditions such that said subject's pain is reduced or eliminated,
    wherein the blue or green spectrum light is of a wavelength between approximately 450-570 nm, and
    wherein said administering comprises contacting an eye of said subject with a material that allows light between approximately 450-570 nm to enter the retina of said subject.

2. The method of claim 1, wherein said material is selected from the group consisting of a contact lens, eye glasses, goggles, or ski goggles.

3. The method of claim 1, wherein said material is a material that filters polluting light of a wavelength that is not between approximately 450-570 nm.

4. The method of claim 1, wherein said subject is contacted with a light source that emits light of a wavelength between approximately 450-570 nm.

5. The method of claim 1, wherein said subject is exposed to broad-spectrum light.

6. The method of claim 1, wherein said light is of a wavelength of 525 nm.

7. The method of claim 1, wherein said light is provided by a light box.

8. The method of claim 1, wherein said administering is administering light of 4 to 500 lux for a time period of 20 minutes to 4 hours per day.

9. The method of claim 1, wherein said administering is performed for a time period of 3 to 10 weeks.

10. The method of claim 1, wherein said administering is 1 hour per day for 3 days.

11. The method of claim 1, wherein said administering is repeated after a gap in time or said administering is continuous.

12. The method of claim 1, wherein said pain is one or more of chronic pain, neuropathic pain, or chronic myalgia.

13. The method of claim 1, wherein said administering results in release of endogenous opioids and cannabinoids selected from endorphins, enkephalins, dynorphins, or endomorphins.

14. The method of claim 1, wherein said administering results in a biological outcome selected from the group consisting of alteration of depolarization-induced $Ca^{2+}$ influx in neurons, alteration of gene expression, or alteration of mu-opioid receptor and cannabinoid receptor I pathways.

15. The method of claim 1, wherein said reduction or reversal of pain persists for at least 1 week after said administering is terminated.

16. The method of claim 1, wherein said reduction or reversal of pain persists for at least 1 month after said administering is terminated.

17. The method of claim 1, wherein said subject is further administered an opioid or non-opioid pain relief medication, wherein a dose of said opioid or non-opioid medication is reduced from a standard dose or from a dose said subject is administered prior to said administering of light.

18. A kit or system, comprising:
    a) a light box, wherein said light box is configured to emit light of approximately 450-570 nm; and
    b) an opioid or non-opioid pain relief medication.

19. The kit or system of claim 18, wherein said opioid or non-opioid pain relief medication is provided at a reduced dose.

20. The kit or system of claim 18, wherein said opioid medication is selected from the group consisting of hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fentanyl, pethidine, Oxycodone, Oxymorphone, methadone, tramadol, Butorphanol, Levorphanol, or propoxyphene.

* * * * *